(12) United States Patent
Murata et al.

(10) Patent No.: US 10,823,718 B2
(45) Date of Patent: Nov. 3, 2020

(54) GAS ALARM, CONTROL DEVICE AND PROGRAM

(71) Applicant: Osaka Gas Co., Ltd., Osaka (JP)

(72) Inventors: Naoyoshi Murata, Hino (JP); Takuya Suzuki, Hachioji (JP); Makoto Okamura, Hachioji (JP); Tsuyoshi Kamioka, Nasushiobara (JP); Hisao Ohnishi, Osaka (JP); Atsushi Nonaka, Hyogo (JP)

(73) Assignee: Osaka Gas Co., Ltd., Osaka (JP)

(*) Notice: Subject to any disclaimer, the term of this patent is extended or adjusted under 35 U.S.C. 154(b) by 0 days.

(21) Appl. No.: 16/393,977

(22) Filed: Apr. 25, 2019

(65) Prior Publication Data

US 2019/0250134 A1 Aug. 15, 2019

Related U.S. Application Data

(63) Continuation of application No. PCT/JP2017/042303, filed on Nov. 24, 2017.

(30) Foreign Application Priority Data

Nov. 25, 2016 (JP) ................................. 2016-229498

(51) Int. Cl.
*G01N 33/00* (2006.01)
*G05D 23/19* (2006.01)
(Continued)

(52) U.S. Cl.
CPC ........... *G01N 33/007* (2013.01); *G01N 27/12* (2013.01); *G05D 23/19* (2013.01); *G08B 17/00* (2013.01); *G08B 21/16* (2013.01)

(58) Field of Classification Search
CPC ........ G08B 29/24; G08B 17/00; G08B 21/16; G01N 33/007; G01N 27/12; G05D 23/19
See application file for complete search history.

(56) References Cited

U.S. PATENT DOCUMENTS 6,651,422 B1* 11/2003 LeGare ................. F01N 11/002
60/274
2016/0084786 A1 3/2016 Suzuki

FOREIGN PATENT DOCUMENTS

| JP | 2009210343 A | 9/2009 |
| JP | 2015046160 A | 3/2015 |
| WO | 2015087906 A1 | 6/2015 |

OTHER PUBLICATIONS

International Search Report for International Patent Application No. PCT/JP2017/042303, issued/mailed by the Japan Patent Office dated Feb. 13, 2018.

(Continued)

*Primary Examiner* — Suman K Nath

(57) ABSTRACT

A gas alarm for detecting a target gas based on a resistance value of a sensor element comprises a measuring unit to measure a characteristic value of the sensor element, a heating control unit to control a heater to perform a heating process to heat the sensor element, a determining unit to determine, based on the characteristic value, whether the sensor element is in a blunt state in which sensitivity of the sensor element is decreased, and an aborting control unit to abort the heating process to determine whether the sensor element is in the blunt state when a characteristic value of the sensor element measured by the measuring unit after beginning of the heating process by the heating control unit meets a predetermined condition.

14 Claims, 17 Drawing Sheets

(51) Int. Cl.
*G08B 21/16* (2006.01)
*G01N 27/12* (2006.01)
*G08B 17/00* (2006.01)

(56) References Cited

OTHER PUBLICATIONS (ISA/237) Written Opinion of the International Search Authority for International Application No. PCT/JP2017/042303, issued/mailed by the International Bureau of WIPO dated Feb. 13, 2018.

* cited by examiner

GAS ALARM, CONTROL DEVICE AND PROGRAM

The contents of the following Japanese patent applications are incorporated herein by reference:
NO. 2016-229498 filed in JP on Nov. 25, 2016, and
NO. PCT/JP2017/042303 filed on Nov. 24, 2017.

BACKGROUND

1. Technical Field

The present invention relates to a gas alarm, a control device and a program.

Traditionally, a gas alarm incorporating a gas sensor has been widely used. When the gas alarm has been used for a long time, a blunting, that is, decreased sensitivity of the gas sensor may happen. As such, a gas alarm capable of detecting the blunting of the gas sensor has been developed (for example, see a Patent Document 1).

2. Related Art

PATENT DOCUMENTS

Patent Document 1: Japanese Patent Application Publication No. 2015-46160

In a gas alarm, it is desirable to prevent detecting of the gas sensor blunting from affecting the accuracy of the main processing for detecting a target gas.

SUMMARY

In the first aspect of the present invention, a gas alarm is provided. The gas alarm may include a sensor element and a heater to heat the sensor element. The gas alarm may detect a target gas based on a characteristic value of the sensor element heated at a detecting process temperature by the heater. A determining unit may determine whether the sensor element is in a blunt state in which sensitivity of the sensor element is decreased. An aborting control unit may abort a heating process to determine whether the sensor element is in the blunt state. The aborting control unit may abort the heating process when a characteristic value of the sensor element measured by a measuring unit after beginning of the heating process by a heating control unit meets a predetermined condition.

The gas alarm may include a sensor element and a heater to heat the sensor element. The gas alarm may detect a target gas based on a resistance value of the sensor element heated to a detecting process temperature by the heater. The gas alarm may comprise a measuring unit, a heating control unit, a first acquiring unit, a determining unit, and an aborting control unit. The measuring unit may measure a resistance value of the sensor element. The heating control unit may control the heater to perform a heating process to heat the sensor element to a first temperature lower than the detecting process temperature. The first acquiring unit may acquire a first resistance value of the sensor element. The first resistance value may be measured by the measuring unit where a temperature of the sensor element reaches the first temperature. The determining unit may determine, based on the first resistance value, whether the sensor element is in a blunt state in which sensitivity of the sensor element is decreased. The aborting control unit may abort the heating process to determine whether the sensor element is in the blunt state. The aborting control unit may abort the heating process when a resistance value of the sensor element measured by the measuring unit after beginning of the heating process by the heating control unit meets a predetermined condition.

A second acquiring unit may acquire a second resistance value of the sensor element. The second resistance value may be measured by the measuring unit where a temperature of the sensor element is a second temperature higher than the first temperature. The determining unit may determine whether the sensor element is in the blunt state based on the first resistance value and the second resistance value.

The determining unit may determine whether the sensor element is in the blunt state by comparing a ratio of the first resistance value to the second resistance value with a predetermined threshold.

The heating control unit may perform a heating control such that a temperature of the sensor element becomes the first temperature after performing a heating control such that a temperature of the sensor element becomes the second temperature. The first acquiring unit may acquire the first resistance value after the second acquiring unit acquires the second resistance value.

The aborting control unit may abort the heating process to determine whether the sensor element is in the blunt state when a resistance value of the sensor element measured by the measuring unit after beginning of the heating process by the heating control unit is equal to or smaller than a predetermined threshold.

A resistance value of the sensor element at the time when the sensor element not in the blunt state is stabilized at the first temperature in a clean environment may be set as the threshold.

A resistance value higher than that of the sensor element at the time when the sensor element not in the blunt state is stabilized at the first temperature in the clean environment may be set as the threshold.

The gas alarm may be capable of setting a plurality of second temperatures. The gas alarm may comprise a memory unit to store different thresholds for each of the plurality of second temperatures.

The aborting control unit may abort the heating process to determine whether the sensor element is in the blunt state based on an inclination of a change in a resistance value of the sensor element over time. A resistance value of the sensor element may be measured by the measuring unit after beginning of the heating process by the heating control unit.

The aborting control unit may abort the heating process to determine whether the sensor element is in the blunt state based on a result of comparing a resistance value of the sensor element measured by the measuring unit after beginning of the heating process by the heating control unit with a previously measured resistance value.

The gas alarm may further comprise a temperature and humidity measurement unit and a correcting unit. The temperature and humidity measurement unit may measure at least one of a temperature and a humidity at or near the gas alarm. The correcting unit may correct the first resistance value and the second resistance value depending on a measurement result by the temperature and humidity measurement unit. The determining unit may determine whether the sensor element is in the blunt state based on a corrected first resistance value and a corrected second resistance value.

In the second aspect of the present invention, a control device is provided. The control device may be a control device in a gas alarm. The gas alarm may include a sensor element and a heater to heat the sensor element. The gas alarm may detect a target gas based on a resistance value of the sensor element heated to a detecting process temperature by the heater. The control device may comprise a measuring unit, a heating control unit, a determining unit, and an aborting control unit. The measuring unit may measure a resistance value of the sensor element. The heating control unit may control the heater to perform a heating process to heat the sensor element to a first temperature lower than the detecting process temperature. The determining unit may determine, based on a characteristic value, whether the sensor element is in a blunt state in which sensitivity of the sensor element is decreased. The aborting control unit may abort the heating process to determine whether the sensor element is in the blunt state. The aborting control unit may abort the heating process when a characteristic value of the sensor element measured by the measuring unit after beginning of the heating process by the heating control unit meets a predetermined condition.

In the third aspect of the present invention, a computer program product having computer instructions, recorded on a non-transitory computer readable medium, for enabling a computer executing the computer instructions to perform operations is provided. The computer may control a gas alarm. The gas alarm may include a sensor element and a heater to heat the sensor element. The gas alarm may detect a target gas based on a characteristic value of the sensor element heated to a detecting process temperature by the heater. The operations may include measuring a characteristic value of the sensor element, controlling the heater to perform a heating process to heat the sensor element, determining, based on the characteristic value, whether the sensor element is in a blunt state wherein sensitivity of the sensor element is decreased, and aborting the heating process to determine whether the sensor element is in the blunt state when a characteristic value of the sensor element measured after beginning of the heating process to determine whether the sensor element is in the blunt state meets a predetermined condition.

The above-mentioned summary of the invention does not list all the necessary features thereof. The invention may also reside in a sub-combination of the features.

DESCRIPTION OF EXEMPLARY EMBODIMENTS

Herebelow, the present invention shall be explained by means of embodiments of the invention, but the following embodiments should not be considered to limit the invention of the claims. Moreover, all the features of the combinations described in the embodiments are not necessarily essential as means for solving the problems of the invention.

Figure 1:
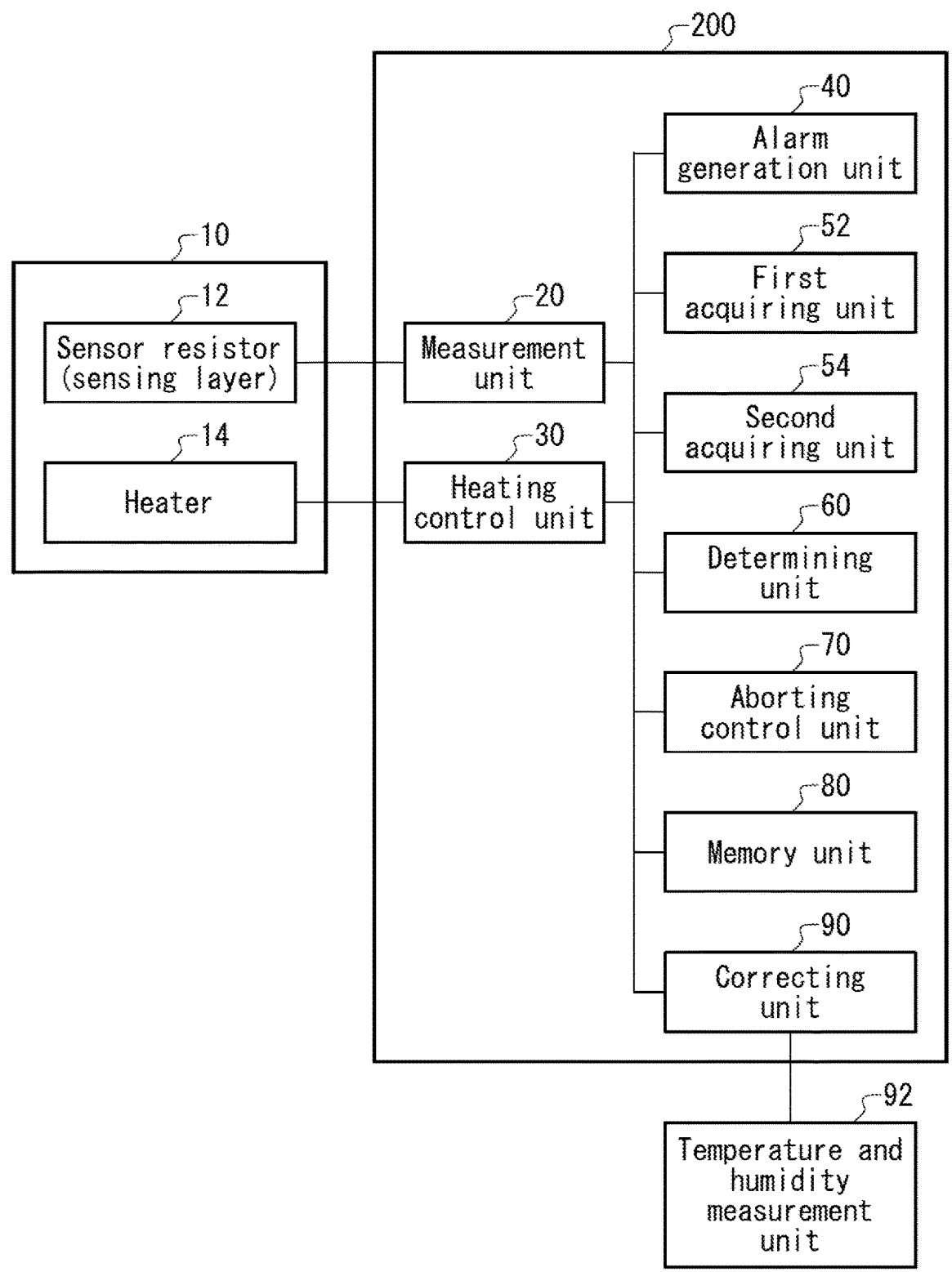
FIG. 1 is a schematic diagram showing a gas alarm 100 according to the first embodiment of the present invention.

FIG. 1 is a schematic diagram showing a gas alarm 100 according to the first embodiment of the present invention. The gas alarm 100 of this example issues an alert when a target gas is detected. The target gas may be a flammable gas. The target gas may be a city gas comprising a methane as the main component, or an LP gas comprising a propane and a butane as the main component. The gas alarm 100 may also be incorporated a CO (carbon monoxide) detecting feature.

The gas alarm 100 comprises a detecting unit 10 and a control device 200. The detecting unit 10 is a gas sensor. The detecting unit 10 comprises a sensor resistor 12 and a heater 14. The sensor resistor 12 is a sensor element. The heater 14 heats the sensor resistor 12. The gas alarm 100 detects the target gas based on a resistance value of the sensor resistor 12 heated to a gas detecting process temperature by the heater 14. A resistance value of the sensor resistor 12 may be referred to as a sensor resistance value. The gas detecting process temperature may be in the range of 350° C. to 450° C., and particularly, about 400° C.

The control device 200 is a control device in the gas alarm 100. The control device 200 comprises a measuring unit 20, a heating control unit 30 and an alarm generation unit 40. The measuring unit 20 measures a sensor resistance value. The measuring unit 20 measures a characteristic value of the sensor element. The characteristic value of the sensor element may be a physical property value or a measurement value associated with the resistance value of the sensor resistor 12. In an example, the measuring unit 20 measures electric voltages at both ends of the sensor resistor 12 when applying an electric current to the sensor resistor 12. In an example, the measuring unit 20 measures an electric current flowing through the sensor resistor 12 when applying an electric voltage to the sensor resistor 12. Measuring the sensor resistance value may include measuring an electric voltage or an electric current corresponding to the sensor resistance value.

The heating control unit 30 controls the heater 14. The heating control unit 30 controls the heater 14 to perform a heating process to heat the sensor resistor 12. The heating control unit 30 may control the heater 14 to heat the sensor resistor 12 to a first temperature lower than the detecting process temperature. The first temperature is preferably, in the range of 150° C. to 300° C., and more preferably, in the range of 200° C. to 280° C. Using the case when the first temperature is 250° C. as an example, this example will be described.

The alarm generation unit 40 issues an alarm when the target gas is detected based on a measurement by the detecting unit 10. The alarm generation unit 40 may also include a feature to broadcast that the detecting unit 10 is in a blunt state and so forth. The alarm generation unit 40 may include an alarm sound output unit to generate a sound like an alarm sound and so forth. The alarm sound output unit may comprise a speaker and a buzzer and the like. The alarm generation unit 40 may comprise an alarm display unit to display alarm states by blinking or lighting light emitting diodes (LEDs) and so forth.

The control device 200 of this example comprises a determining unit 60 and an aborting control unit 70. The control device 200 may comprise a first acquiring unit 52, a second acquiring unit 54, the determining unit 60, and the aborting control unit 70. The first acquiring unit 52 acquires a first resistance value of the sensor resistor 12. The first resistance value is a sensor resistance value measured by the measuring unit 20 where a temperature of the sensor resistor 12 reaches the first temperature. The second acquiring unit 54 acquires a second resistance value of the sensor resistor 12. The second resistance value is a sensor resistance value measured by the measuring unit 20 where a temperature of the sensor resistor 12 is the second temperature. The second temperature may be in the range of 350° C. to 450° C., and particularly, about 400° C. The second temperature may be the above-mentioned detecting process temperature for detecting the target gas.

The determining unit 60 determines whether the detecting unit 10 is in the blunt state. The blunt state is a state where sensitivity of the detecting unit 10 as a gas sensor is decreased, and more specifically, a state where sensitivity of the sensor resistor 12 to detect the target gas is decreased. When the sensor resistor 12 becomes in the blunt state, it is desirable to replace the detecting unit 10 of the gas alarm 100 with a normal product. The determining unit 60 may determine whether the detecting unit 10 is in the blunt state or not based on a specific value (a first specific value) measured by the measuring unit 20 where a temperature of the sensor resistor 12 reaches the first temperature lower than the detecting temperature. In particular, the determining unit 60 may determine whether the detecting unit 10 is in the blunt state or not based on at least the first resistance value.

The aborting control unit 70 aborts the heating process to determine whether the sensor resistor 12 is in the blunt state when the gas alarm 100 is in an environment which is not appropriate to determine as to the blunt state. The aborting control unit 70 aborts the heating process to determine whether the sensor resistor 12 is in the blunt state when a characteristic value of the sensor resistor 12 measured by the measuring unit 20 after beginning of the heating process meets a predetermined condition. More specifically, the aborting control unit 70 may abort the heating process to determine whether the sensor resistor 12 is in the blunt state when a resistance value of the sensor resistor 12 measured by the measuring unit 20 after beginning of the heating process by the heating control unit 30 meets a predetermined condition.

The control device 200 may further comprise a memory unit 80 and a correcting unit 90. Moreover, the gas alarm 100 may comprise a temperature and humidity measurement unit 92. The temperature and humidity measurement unit 92 measures at least one of a temperature and a humidity at or near the gas alarm 100. The correcting unit 90 may correct the first resistance value and the second resistance value depending on a measurement result by the temperature and humidity measurement unit 92. The memory unit 80 may store reference values such as a threshold.

Figure 2:
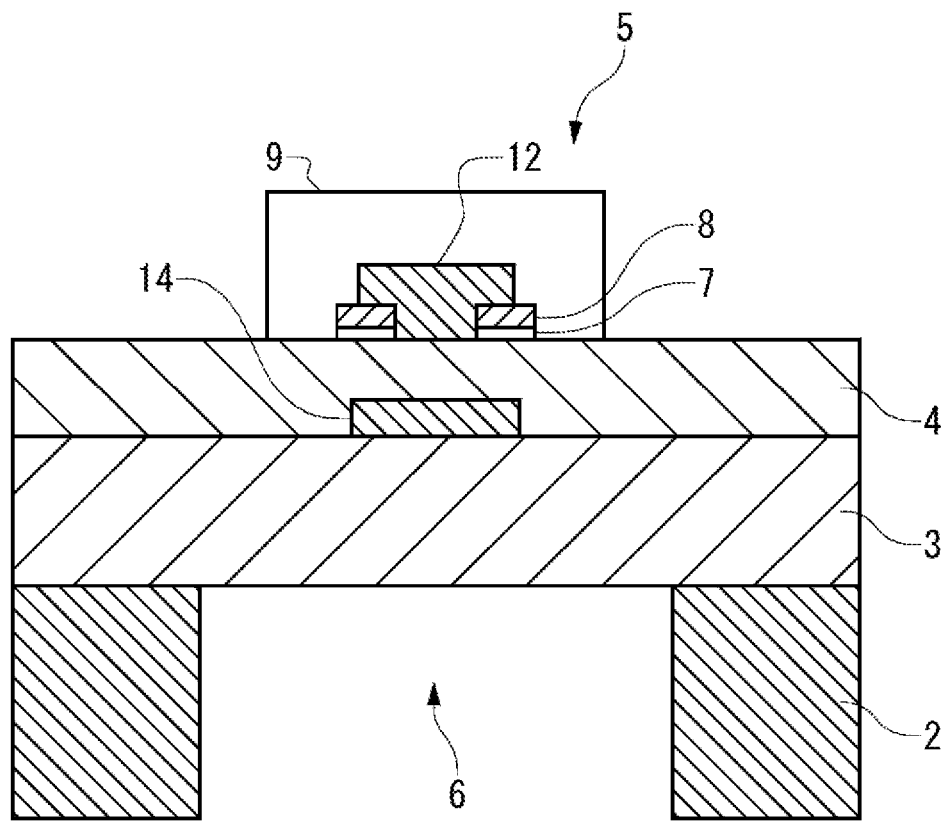
FIG. 2 is a cross-sectional view showing a schematic configuration of a detecting unit 10.

FIG. 2 is a cross-sectional view showing a schematic configuration of the detecting unit 10. The detecting unit 10 of this example is a thin film micro sensor. The detecting unit 10 of this example comprises a silicon substrate 2, a thermal insulating support layer 3, a heater layer to function as the heater 14, an electrical insulating layer 4, and a gas sensing layer 5. The silicon substrate 2 has a through-hole 6 provided thereon. The gas sensing layer 5 comprises a joint layer 7, an electrode of the gas sensing layer 8, a sensor resistor 12, and a selective combustion layer 9. The sensor resistor 12 is formed as a sensing layer comprising a metal oxide such as, for example, $SnO_2$, $In_2O_3$, $WO_3$, ZnO or $TiO_2$ as the main component.

The selective combustion layer 9 is a sintered compact carrying at least one catalyst of Pd, PdO, Pt and so forth, for example. In an example, the selective combustion layer 9 may be an $Al_2O_3$ sintered compact carrying a catalyst and may be formed comprising a metal oxide such as $Cr_2O_3$, $Fe_2O_3$, $Ni_2O_3$, $ZrO_2$, $SiO_2$, and zeolite as the main component. The silicon substrate 2 is composed of a silicon wafer. The heater 14 heats the gas sensing layer 5. The detecting unit 10 detects the target gas based on a resistance value of the sensor resistor 12 when the sensor resistor 12 (the sensing layer) is heated by the heater 14 (the heater layer).

Figure 3:
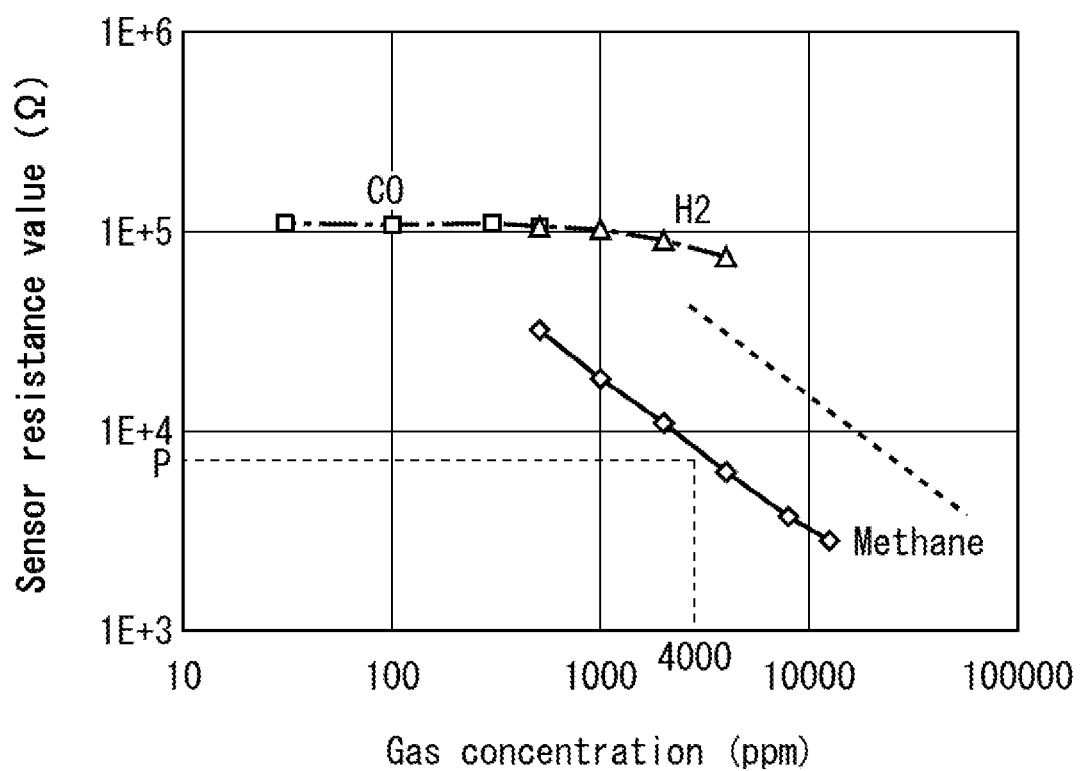
FIG. 3 is a diagram showing a relationship between a sensor resistance value and a gas concentration.

FIG. 3 is a diagram showing a relationship between a sensor resistance value and a gas concentration. The blunt state is described with reference to FIG. 3. A change in each sensor resistance value for each gas of CO (carbon monoxide), $H_2$ (hydrogen) and methane relative to a change in the gas concentration (ppm) is shown. For each characteristic of CO (carbon monoxide) and $H_2$ (hydrogen), those are respectively indicated by dashed lines. In contrast, for methane as the target gas, a characteristic of the detecting unit 10 in non-blunt state is indicated by a solid line and a characteristic of the detecting unit 10 in the blunt state is indicated by a dotted line.

As indicated by the dashed lines in the figure, for CO (carbon monoxide) and $H_2$ (hydrogen), the sensor resistance value is nearly unchanged as the gas concentration increases. In contrast, as indicated by the solid line and dotted line in the figure, for methane, the sensor resistance value decreases as the gas concentration increases regardless of whether the detecting unit 10 is in the blunt state or not. However, for the detecting unit 10 in the blunt state, a gas concentration corresponding to any sensor resistance value is higher when compared with the detecting unit 10 in the non-blunt state.

For example, in the case where a gas leakage alarm should be issued when the gas concentration of methane exceeds 4000 ppm, a sensor resistance value P corresponding to 4000 ppm based on the characteristic of the detecting unit 10 in the non-blunt state is set as a threshold to determine the gas leak. An alarm is issued when a sensor resistance value at the detecting process temperature is below the threshold P. However, when the detecting unit 10 is in the blunt state, the gas concentration of methane already reaches about 20000 ppm when the sensor resistance value is below P. Hence, when the detecting unit 10 in the blunt state, since the gas leakage alarm will not be issued until the gas concentration of methane reaches a higher value than usual, such as 20000 ppm, the alarm issuance may be delayed.

Figure 4:
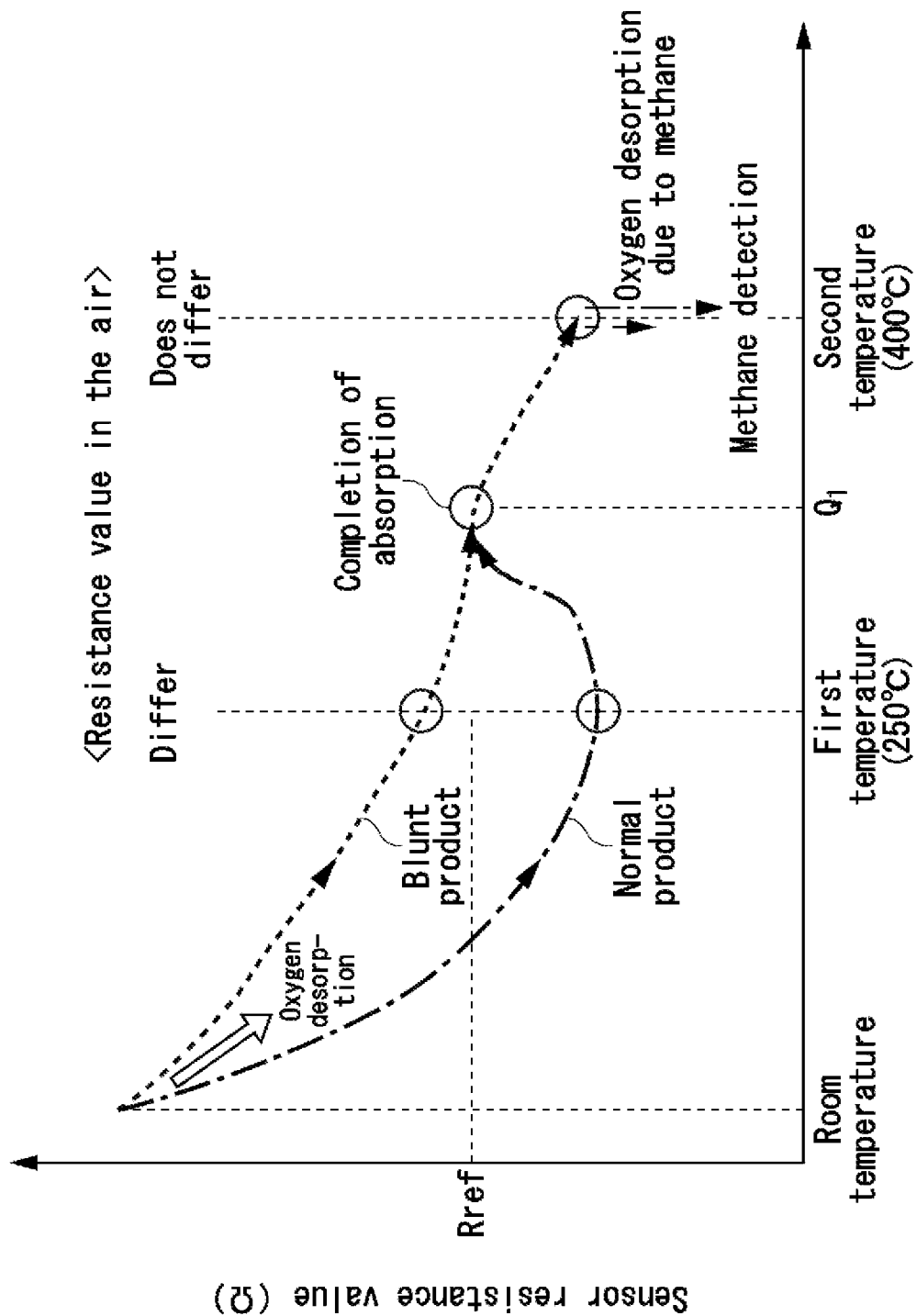
FIG. 4 is a diagram showing a temperature characteristic of the sensor resistance value.

FIG. 4 is a diagram showing a temperature characteristic of the sensor resistance value. In FIG. 4, the characteristic of the gas alarm 100 in the non-blunt state, i.e., a normal product is indicated by a dashed line. The characteristic of the gas alarm 100 in the blunt state, i.e., a blunt product is indicated by a dotted line. Each characteristic indicated by the dashed line and dotted line show a relationship between a sensor resistance value and a temperature when a temperature of the sensor resistor 12 is raised from the room temperature to 400° C. by pulse-driving, in a cycle ranging from 30 sec to 60 sec, the heater 14 with a pulse width in the range of 50 ms to 300 ms.

In the normal gas alarm 100 in the non-blunt state, when a temperature of the sensor resistor 12 is raised from the room temperature, the sensor resistance value decreases between the room temperature and the first temperature as the temperature rises. In the gas alarm 100 as the blunt product as well, the sensor resistance value decreases between the room temperature and the first temperature as the temperature rises. However, as shown in the figure, a drop rate of the sensor resistance value of the blunt gas alarm 100 is lower than that of the normal gas alarm 100 in the non-blunt state. Thus, at the first temperature, for example, around 250° C., the sensor resistance value of the blunt product is larger than that of the non-blunt state. In the example shown, the sensor resistance value of the blunt product is more than twice that of the normal product.

The reason why the sensor resistance value decreases in the temperature area between the room temperature and the first temperature is ascribed to oxygen desorption ($O^-$ desorption) caused as the temperature rises. When a temperature of the sensor resistor 12 further rises beyond the first temperature, for the normal product, the sensor resistance value then increases as the temperature rises, as indicated by the dashed line. However, as shown, the sensor resistance value decreases in the temperature area between the temperature $Q_1$ and the second temperature (for example, 400° C.) as the temperature rises.

The reason why the sensor resistance value increases in the temperature area between the first temperature and the temperature $Q_1$ is ascribed to oxygen absorption ($O^{2-}$ absorption) caused on the sensing layer constituting the sensor resistor 12. When absorbed on the sensing layer, oxygen is absorbed thereon in its ionic form ($O^{2-}$) depriving an electron from the sensing layer. This increases the resistance value of the sensing layer. Oxygen absorption ends at the temperature $Q_1$ and thereafter the sensor resistance value is considered to decrease due to characteristics of a semiconductor material of the sensing layer such as $SnO_2$ and so forth as the temperature rises.

In contrast, as indicated by the dotted line, the sensor resistance value of the blunt product shows a characteristic such that the sensor resistance value is nearly unchanged at the temperature area between the first temperature and the temperature $Q_1$ or decreases as the temperature rises. The blunt product also shows the characteristic similar to that of the non-blunt product at the temperature area between the temperature $Q_1$ and the second temperature. And the sensor resistance value of the blunt product at the second temperature is almost the same as that of the normal product in the non-blunt state. The determining unit 60 of this example determines whether the detecting unit 10 is in the blunt state using a temperature characteristic of the sensor resistance value as described above.

The determining unit 60 may determine whether the sensor resistor 12 is in the blunt state in which sensitivity of the sensor resistor 12 is decreased based on the first resistance value. More specifically, the determining unit 60 may determine that the sensor resistor 12 is in the blunt state when the first resistance value is equal to or greater than the threshold. The determining unit 60 may determine that the detecting unit 10 is in the blunt state when the first resistance value measured at this time is greater than the first resistance value at delivery or at the previous measurement by a given value or more. Moreover, the determining unit 60 may determine whether the detecting unit 10 is in the blunt state based on the first resistance value and the second resistance value.

In particular, the second resistance value at the second temperature in the range of 350° C. to 450° C. is not changed significantly regardless of the presence or absence of the blunt state. On the contrary, for the blunt product, the first resistance value is higher at the first temperature in the range of 200° C. to 280° C. when compared with the non-blunt product. Accordingly, the determining unit 60 may determine whether the detecting unit 10 is in the blunt state or not by comparing a ratio of the first resistance value to the second resistance value with a predetermined threshold.

The above-mentioned characteristics shown in FIG. 4 show a change in the sensor resistance value in the air. Thus, an accurate determination as to the blunt state is not possible when a miscellaneous gas exists in the air. The miscellaneous gas means a gas other than the target gas including a methane, a propane, a butane, and a CO, and more specifically, the miscellaneous gas may be a low-boiling hydrocarbon. The miscellaneous gas is an alcohol such as, for example, an ethanol, a methanol, an isopropyl alcohol and so forth, an ammonia, a sulfur or a hydrogen. When the sensor resistor 12 is heated to the second temperature higher than the first temperature, the miscellaneous gas is combusted in the selective combustion layer 9 even when the miscellaneous gas exists at or near the detecting unit 10. Thus, the sensor resistor 12 is less affected by the miscellaneous gas when heated to the second temperature when compared with when heated to the first temperature.

On the contrary, when the sensor resistor 12 is heated to the first temperature under the atmosphere where the miscellaneous gas exists at or near the detecting unit 10, the miscellaneous gas is not combusted enough in the selective combustion layer 9, reaching the surface of the sensor resistor 12 thus affecting the sensor resistor 12. More specifically, at the first temperature, the miscellaneous gas causes oxygen ions ($O^{2-}$) absorbed on the surface of the sensing layer functioning as the sensor resistor 12 to desorb excessively. Accordingly, it takes longer for the oxygen ions ($O^{2-}$) to be absorbed on the surface of the sensing layer again, thereby resulting in potential errors when the detecting unit 10 detects the target gas.

In the gas alarm 100 of this example, the aborting control unit 70 aborts the heating process when the resistance value of the sensor element meets a predetermined condition. The aborting control unit 70 controls the heating process not to affect excessively. Hence, it can prevent errors from occurring when the detecting unit 10 detects the target gas.

Using the state where the oxygen ions ($O^{2-}$) are absorbed on the surface of the sensor resistor 12 as a reference, the detecting unit 10 detects a change in the sensor resistance value due to an oxygen ion desorption by the target gas such as a methane and so forth. When a small amount of oxygen ion ($O^{2-}$) is absorbed on the surface of the sensor resistor 12 under the influence of the miscellaneous gas, the sensor resistance value becomes small despite the absence of the target gas such as a methane and so forth. As a result, the gas leakage alarm may be issued despite the absence of the target gas.

In the gas alarm 100 of this example, the aborting control unit 70 aborts the heating process to the first temperature when the miscellaneous gas exists at or near the detecting unit 10. The aborting control unit 70 controls such that the miscellaneous gas causes the oxygen ions ($O^{2-}$) absorbed on the surface of the sensing layer not to desorb excessively. Therefore, this can prevent the sensor resistance value from becoming small despite the absence of the target gas such as a methane and so forth, and can also prevent the gas leakage alarm from being issued despite the absence of the target gas.

Figure 5:
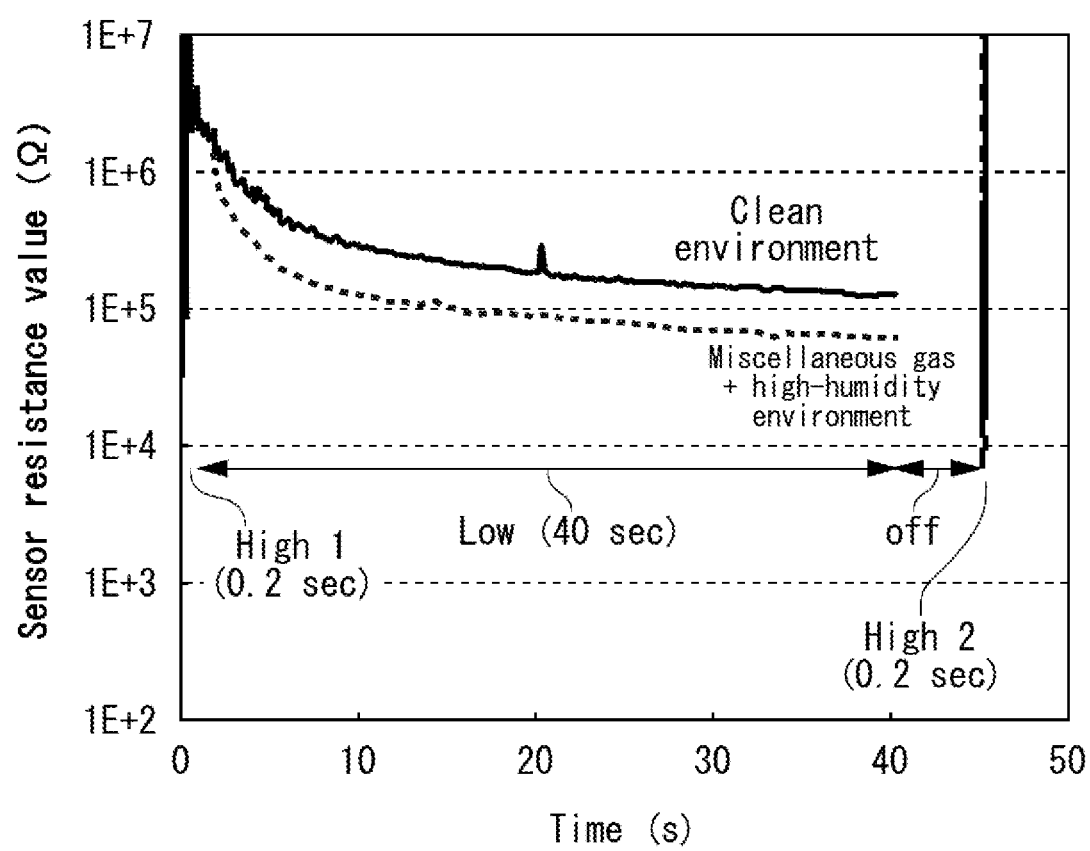
FIG. 5 is a diagram showing a change in a resistance value of a sensor resistor 12 heated by a heater 14.

FIG. 5 is a diagram showing a change in the resistance value of the sensor resistor 12 heated by the heater 14. In FIG. 5, a change in the sensor resistance value in a clean environment is indicated by a solid line and a change in the sensor resistance value in an environment including the miscellaneous gas is indicated by a dotted line. In an environment including the miscellaneous gas, a high-humidity environment and an environment including the miscellaneous gas and being high-humidity, respectively, similar tendencies are shown as indicated by the dotted line in FIG. 5.

The heating control unit 30 performs a heating control by driving the heater 14 with a pulse width in the range of 50 ms to 300 ms in the High_1 area such that a temperature of the sensor resistor 12 becomes the second temperature. In an example, the heating control unit 30 heats the sensor resistor 12 to 400° C. by pulse-driving the heater 14 with a pulse width of 200 ms. Then the heating control unit 30 performs a heating control by driving the heater 14 for a time period ranging from 30 sec to 60 sec in the Low area such that a temperature of the sensor resistor 12 becomes the first temperature. In this example, a heating period in the Low area is set to 40 seconds. The heating control in the Low area is a heating control to heat the sensor resistor 12 to the first temperature in order to determine whether the detecting unit 10 is in the blunt state.

The heating control unit 30 turns off the heating control for five seconds after the Low area. The heating control unit 30 then performs a heating control by driving the heater 14 with a pulse width in the range of 50 ms to 300 ms in the High_2 area again such that a temperature of the sensor resistor 12 becomes the second temperature. As shown in FIG. 5, in the course of the heating control from the second temperature in the High_1 area to the first temperature in the Low area, the sensor resistance value under the atmosphere where the miscellaneous gas exists shows a smaller value than the sensor resistance value under the clean environment where an amount of miscellaneous gas does not exceed a given value.

Figure 6:
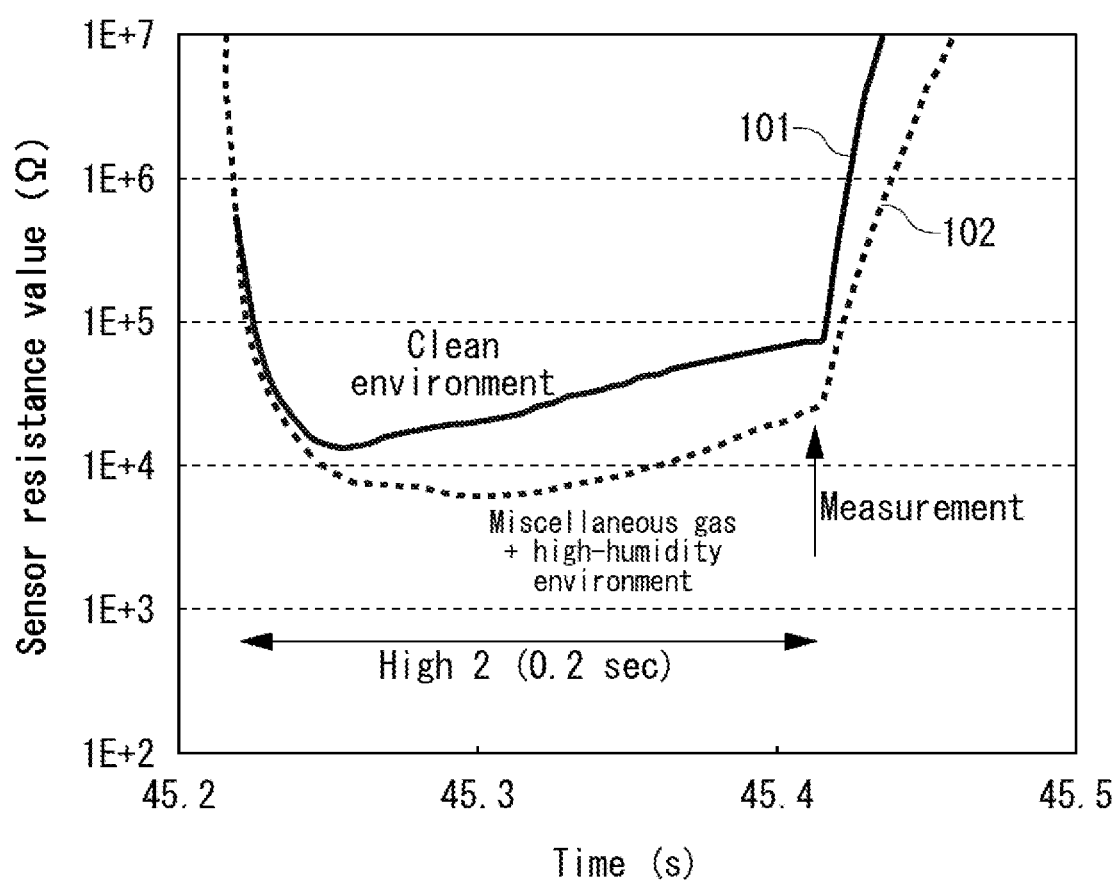
FIG. 6 is an enlarged view of the High area of FIG. 5.

FIG. 6 is an enlarged view of the High area of FIG. 5. As described earlier, the sensor resistance value decreases in the temperature area of the second temperature as the temperature rises. Hence, heating the sensor resistor 12 to the second temperature by pulse-driving the heater 14 with a pulse width in the range of 50 ms to 300 ms decreases the sensor resistance value showing a temperature characteristic of downward convex. In FIG. 6, a sensor resistance value is measured at the final timing of driving the heater. Then, the target gas is detected based on the sensor resistance value measured.

However, after the heating process to determine as to the blunt state is performed in the environment where the miscellaneous gas exits, the oxygen ions ($O^{2-}$ absorbed on the surface of the sensing layer functioning as the sensor resistor 12 desorbs excessively. Thus, as shown in FIG. 6, in the sensor resistance characteristic 102 of the gas alarm 100 in which the heating process to determine as to the blunt state is performed in the environment where the miscellaneous gas exits, the sensor resistance value drops too low to recover even by heating the sensor resistor 12 for about 200 ms. On the contrary, in the sensor resistance characteristic 101 of the gas alarm 100 in which the heating process to determine as to the blunt state in the clean environment is performed, the sensor resistance value recovers to $1 \times 10^5 \Omega$ by heating the sensor resistor 12 for about 200 ms. Therefore, errors do not occur in detecting the target gas based on the sensor resistance value.

In the gas alarm 100 of this example, the aborting control unit 70 aborts the heating process to the first temperature when the miscellaneous gas exists at or near the detecting unit 10. This prevents the oxygen ions ($O^{2-}$) absorbed on the surface of the sensing layer functioning as the sensor resistor 12 from desorbing excessively. The aborting control unit 70 may also abort the heating process to the first temperature when the surrounding at or near the detecting unit 10 is highly humid.

Figure 7:
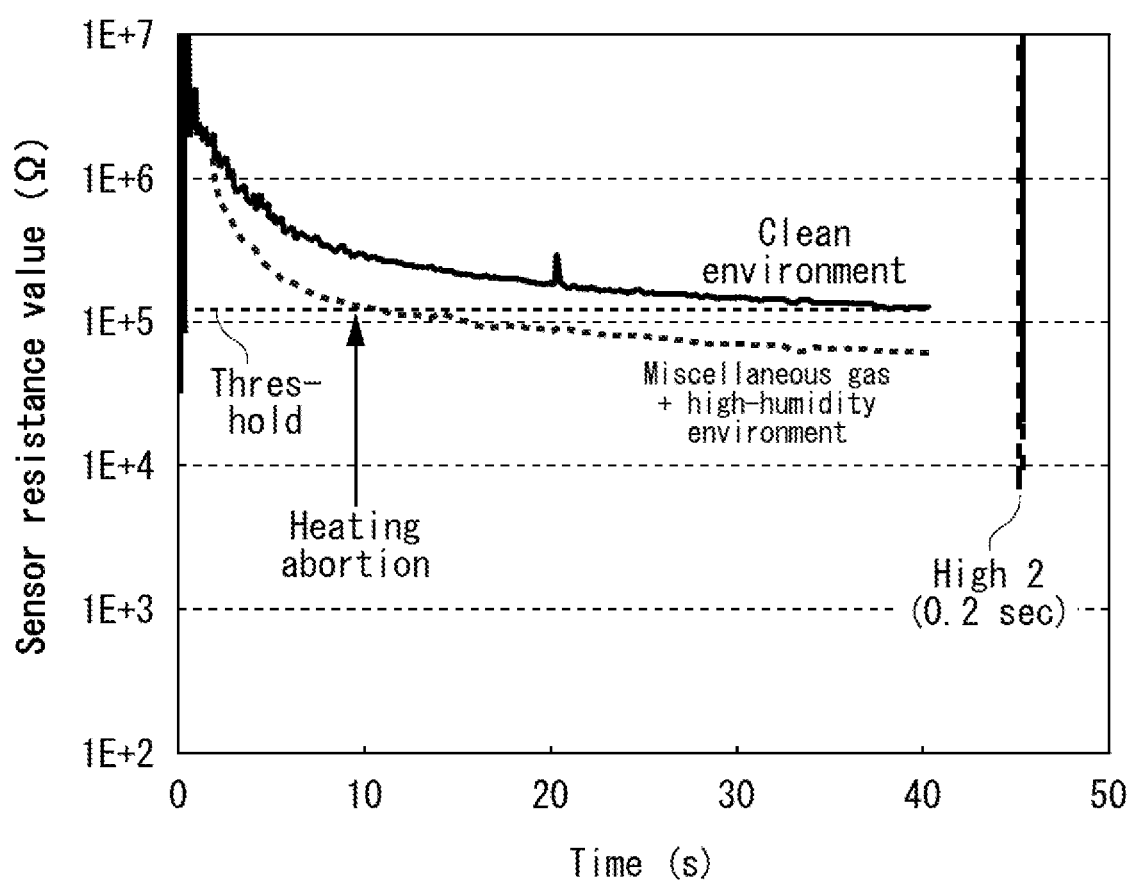
FIG. 7 is a diagram showing an aborting process to abort a heating process.

FIG. 7 is a diagram showing an aborting process to abort the heating process. FIG. 7 is a diagram showing a change in the sensor resistance value of the sensor resistor 12 heated by the heater 14. In FIG. 7, a change in the sensor resistance value in a clean environment is indicated by a solid line and a change in the sensor resistance value in an environment including the miscellaneous gas is indicated by a dotted line. In this example, the aborting control unit 70 aborts the heating process to determine whether the sensor resistor 12 is in the blunt state when a resistance value of the sensor resistor 12 measured by the measuring unit 20 after beginning of the heating process by the heating control unit 30 is equal to or smaller than the predetermined threshold.

A sensor resistance value Rref of the sensor resistor 12 at the time when the sensor resistor 12 in the non-blunt state is stabilized at the first temperature in the clean environment may be set as the threshold. By setting the threshold in this manner, it enables to detect the miscellaneous gas generating in the surrounding at an early stage and abort the heating process to the first temperature thereby mitigating the influence on the subsequent process of detecting the target gas. A resistance value higher than the above-mentioned sensor resistance value Rref may also be set as the threshold. By setting the threshold in this manner, it enables to detect the miscellaneous gas generating in the surrounding at an earlier stage and abort the heating process to the first temperature.

Figure 8:
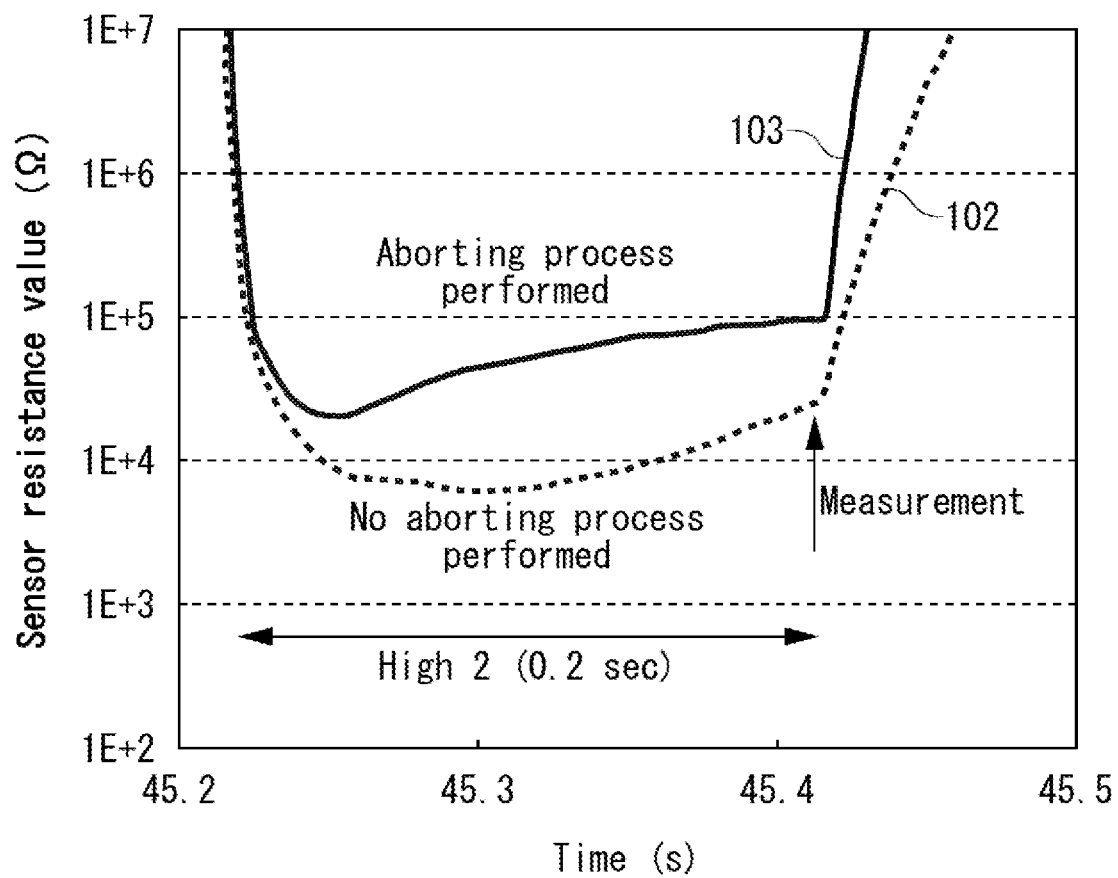
FIG. 8 is an enlarged view of the High area of FIG. 7.

FIG. 8 is an enlarged view of the High_2 area of FIG. 7. FIG. 8 shows a change in the sensor resistance value in the environment including the miscellaneous gas. In FIG. 8, the sensor resistance characteristic 102 of the sensor resistance value of the gas alarm 100 in which the heating process was not aborted is indicated by a dotted line and the sensor resistance characteristic 103 of the gas alarm 100 in which the heating process was aborted is indicated by a solid line. The sensor resistance characteristic 102 of the gas alarm in which the heating process was not aborted is the same as the sensor resistance characteristic 102 of the gas alarm 100 of FIG. 6 in which the heating process to determine as to the blunt state was performed in the environment where the miscellaneous gas exists.

As shown in FIG. 8, in the sensor resistance characteristic 103 of the sensor resistance value of the gas alarm 100 in which the heating process was aborted, the sensor resistance value recovers to $1 \times 10^5 \Omega$ by heating the sensor resistor 12 for about 200 ms. Therefore, in the course of the heating process to the first temperature, the aborting control unit 70 aborts the heating process when the first resistance value is below the predetermined threshold thereby enabling to prevent the oxygen ions ($O^{2-}$) absorbed on the surface of the sensing layer functioning as the sensor resistor 12 from desorbing excessively. Thus, it can mitigate the influence on the subsequent process of detecting the target gas.

Figure 9:
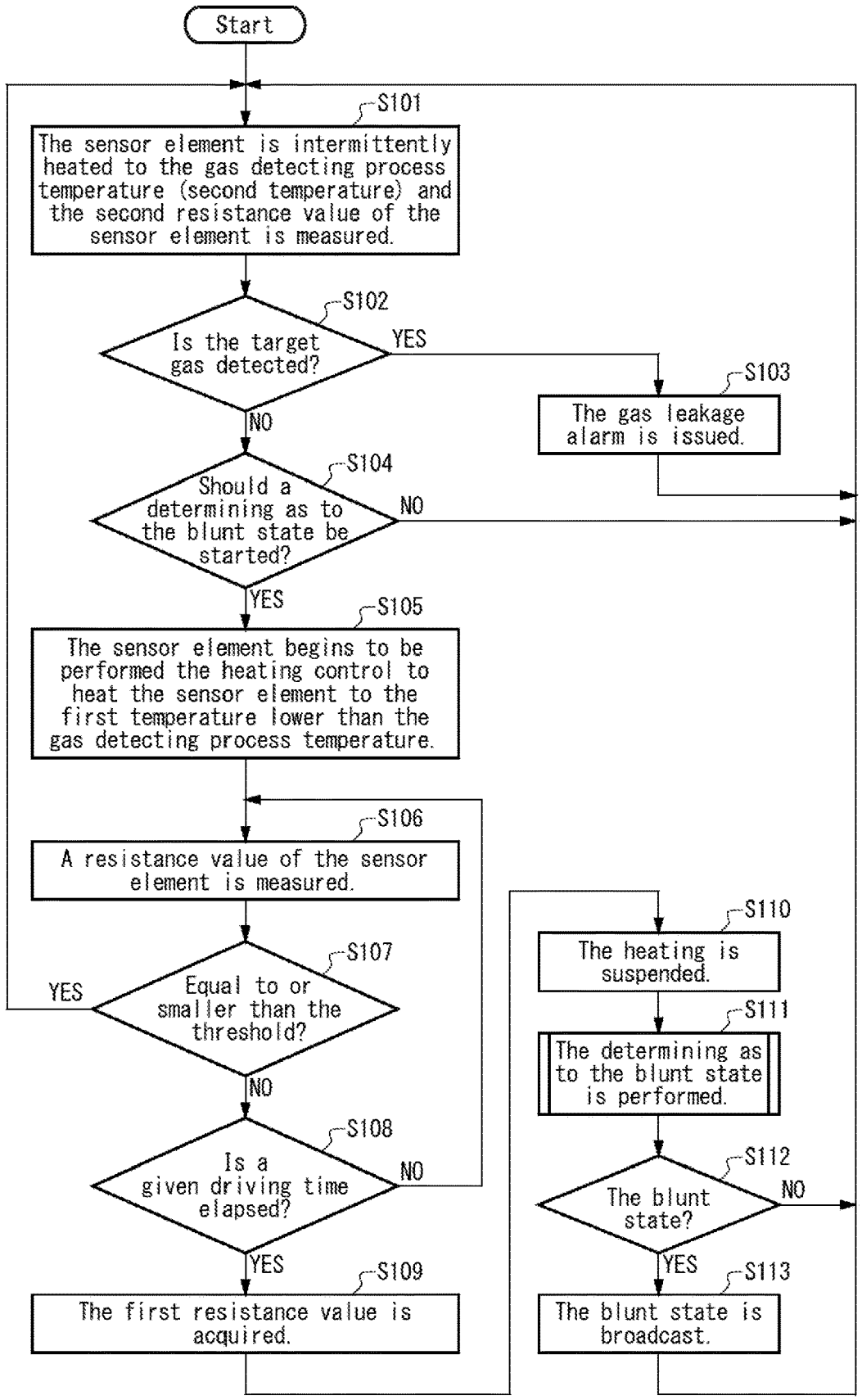
FIG. 9 is an example of a flow chart showing a process by the gas alarm 100 according to the first embodiment of the present invention.

FIG. 9 is an example of a flow chart showing a process by the gas alarm 100 according to the first embodiment of the present invention. The heating control unit 30 heats the sensor resistor 12 intermittently until a temperature of the sensor resistor 12 reaches the gas detecting process temperature. The gas detecting process temperature may be the second temperature. The second acquiring unit 54 acquires the second resistance value (Step S 101). If the second resistance value is below the predetermined threshold, the target gas being determined to be detected (Step S 102: YES), the alarm generation unit 40 issues the gas leakage alarm (Step S 103). If the second resistance value is equal to or greater than the threshold, the target gas being determined not to be detected (Step S 102: NO), the process proceeds to the Step S 104.

Moreover, if the concentration of the target gas is equal to or smaller than the predetermined concentration, the target gas may be determined not to be detected. At Step S 104, the determining unit 60 determines whether a determining as to the blunt state should be started to run. The determining unit 60 may perform the determining as to the blunt state on a regular basis. The determining unit 60 runs the determining as to the blunt state at a given time once a day, for example. However, note that frequency of running the determining as to the blunt state is not limited in this respect. Following the detecting of the target gas, the determining as to the blunt state may be performed at every cycle or at other frequencies.

If the determining unit 60 determines that the determining as to the blunt state should not be started to run (Step S 104: NO), the process returns to the Step S 101 without performing the sensor diagnosis process for determining as to the blunt state. Then in a cycle ranging from 30 sec to 60 sec, for example, the heater 14 is pulse-driven with a pulse width in the range of 50 ms to 300 ms again. The heating control unit 30 waits until when the determining as to the blunt state should be started to run (Step S 104: YES), and begins to perform the heating control for the heater 14 to heat the sensor resistor 12 (the sensor element) to the first temperature lower than the detecting process temperature (Step S 105).

In this example, the heating control unit 30 may perform the heating control such that a temperature of the sensor resistor 12 becomes the first temperature (Step S 105) after performing the heating control such that a temperature of the sensor resistor 12 becomes the second temperature (Step S 101). The first acquiring unit 52 may acquire the first resistance value after the second acquiring unit 54 acquires the second resistance value. In this manner, the existence of the miscellaneous gas may be detected more easily by first heating the sensor resistor 12 to the second temperature so as to have oxygen absorbed ($O^{2-}$ absorption) on the surface of the sensing layer of the sensor resistor 12, performing the heating control to the first temperature and then evaluating the influence of the miscellaneous gas. However, note that heating profile is not limited in this respect. For example, after performing a temperature control to the first temperature, the heating control unit 30 may control such that a temperature of the sensor resistor 12 becomes a temperature lower than the first temperature in order to detect CO.

After the heating control to the first temperature is begun, the measuring unit 20 still measures a sensor resistance value of the sensor resistor 12 (Step S 106). The aborting control unit 70 aborts the heating process to determine whether the sensor resistor 12 is in the blunt state if a sensor resistance value of the sensor resistor 12 measured by the measuring unit 20 after beginning of the heating process by the heating control unit 30 is equal to or smaller than the predetermined threshold (Step S 107: YES). The process returns to the Step S 101. Accordingly, this can stop the heating process from being continued at the first temperature where the miscellaneous gas cannot be combusted enough in the selective combustion layer 9. This can also prevent the oxygen ions ($O^{2-}$) absorbed on the surface of the sensing layer of the sensor resistor 12 from desorbing excessively. On the other hand, at Step S 101, since the sensor resistor 12 is heated to the gas detecting process temperature (the second temperature) higher than the first temperature, the miscellaneous gas is combusted in the selective combustion layer 9 even if the miscellaneous gas exists at or near the detecting unit 10. Therefore, the influence of the miscellaneous gas on the sensor resistor 12 can be ignored.

If a sensor resistance value of the sensor resistor 12 measured by the measuring unit 20 after beginning of the heating process by the heating control unit 30 is greater than the predetermined threshold (Step S 107: NO), any particular problems will not occur if the heating control to the first temperature is continued. Hence, waiting until when a predetermined heater driving time is elapsed (Step S 108: YES), the first acquiring unit 52 acquires a sensor resistance value measured by the measuring unit 20 where a temperature of the sensor resistor 12 reaches the first temperature as the first resistance value (Step S 109). The heating control unit 30 may suspend the heating (Step S 110).

The determining unit 60 then performs the determining as to the blunt state (Step S 111). As a result of the determining as to the blunt state, if the detecting unit 10 is determined to be in the non-blunt state (Step S 112: NO), there are not any particular problems, so the process returns to the Step S 101. On the contrary, if the detecting unit 10 is determined to be in the blunt state (Step S 112: YES), the alarm generation unit 40 broadcasts that the detecting unit 10 is in the blunt state by an indication lump, a buzzer and so forth (Step S 113).

Figure 10:
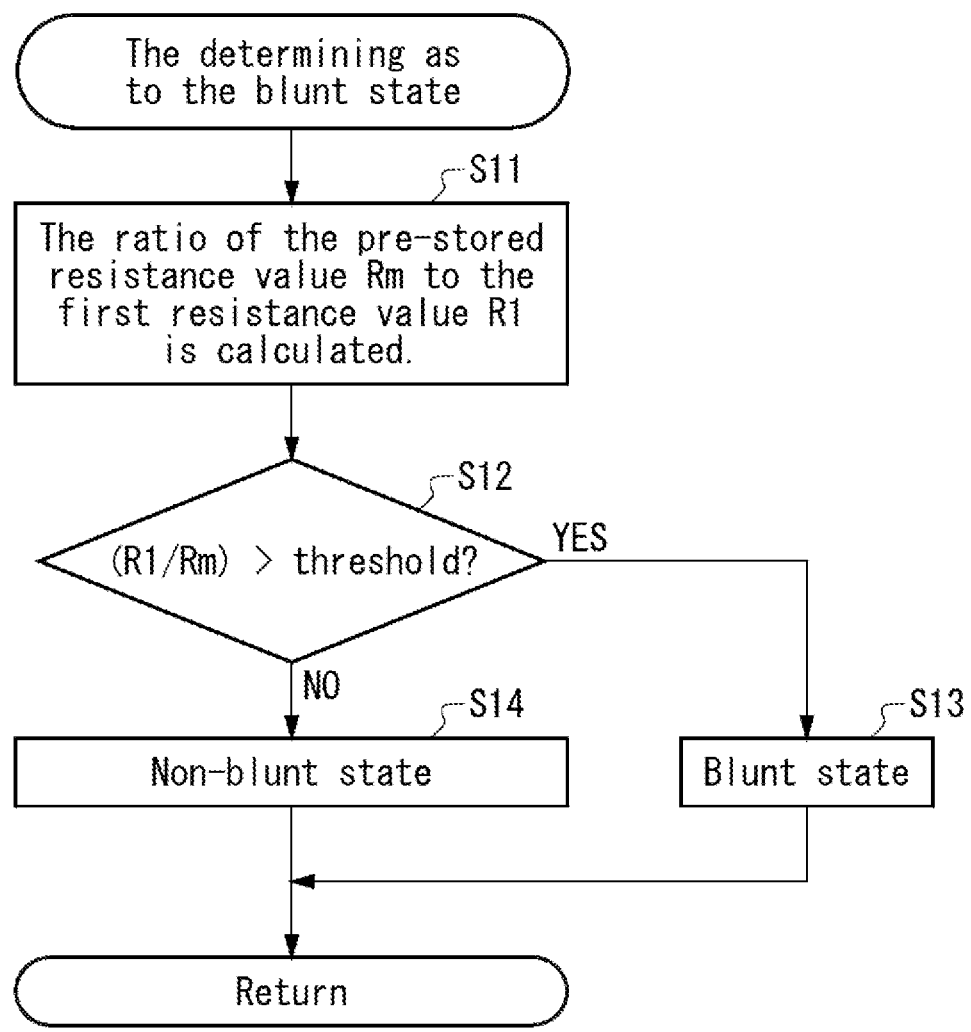
FIG. 10 is an example of a flow chart showing an example of a determining as to the blunt state by the gas alarm 100.

FIG. 10 is a flow chart showing an example of a determining as to the blunt state by the gas alarm 100. That is, FIG. 10 shows an example of the determining as to the blunt state at Step S 111 of FIG. 9. In the gas alarm 100 of this example, the first resistance value measured at delivery of the gas alarm 100, for example, is stored beforehand as a reference resistance value Rm in the memory unit 80.

The determining unit 60 determines whether the sensor resistor 12 is in the blunt state in which sensitivity of the sensor resistor 12 is decreased based on the first resistance value. As an example, the determining unit 60 calculates a ratio (R1/Rm) of the first resistance value currently acquired to the reference resistance value Rm (Step S 11). The determining unit 60 determines whether the R1/Rm is greater than a given threshold (Step S 12). The determining unit 60 determines that the detecting unit 10 is in the blunt state (Step S 13) if the R1/Rm is greater than the given threshold (Step S 12: YES). On the contrary, the determining unit 60 determines that the detecting unit 10 is not in the blunt state (Step S 14) if the R1/Rm is equal to or smaller than the given threshold (Step S 12: NO).

Figure 11:
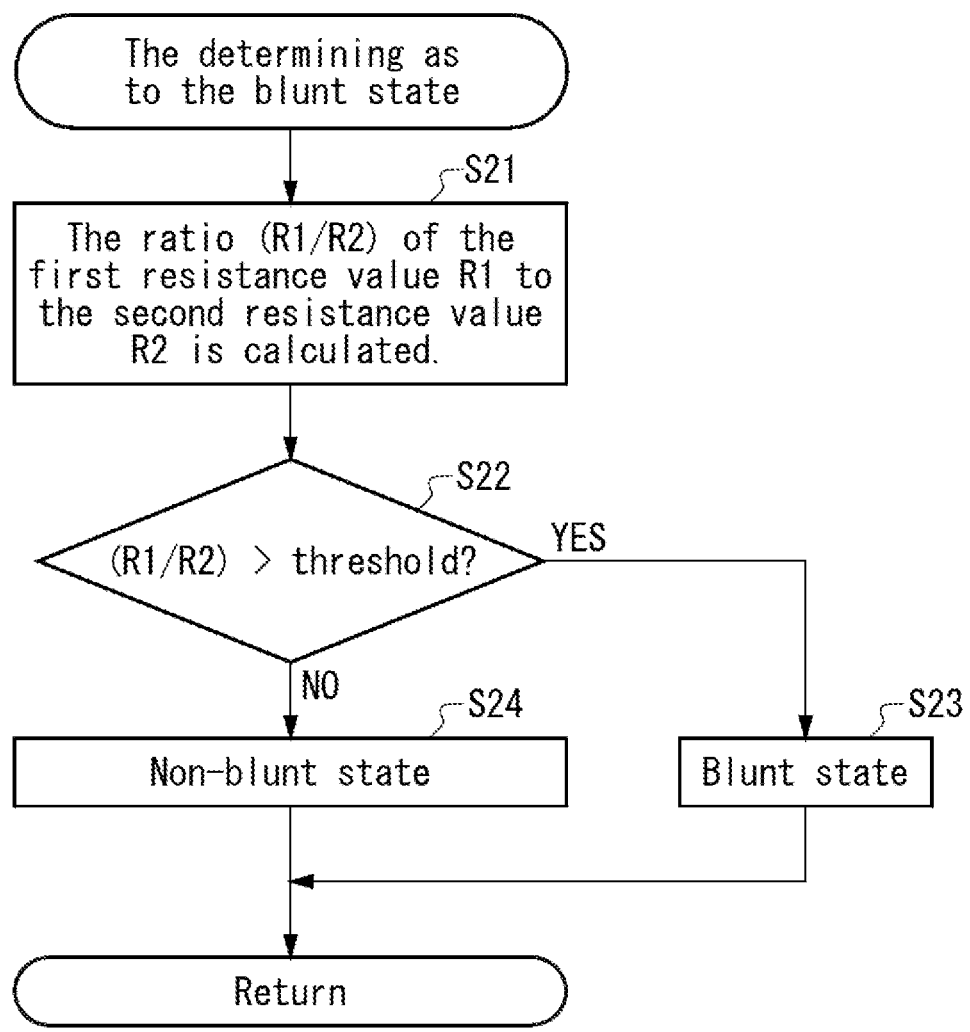
FIG. 11 is a flow chart showing another example of a determining as to the blunt state by the gas alarm 100.

FIG. 11 is a flow chart showing another example of a determining as to the blunt state by the gas alarm 100. FIG. 11 shows another example of the determining as to the blunt state at Step S 111 of FIG. 9. The determining unit 60 may determine whether the sensor resistor 12 is in the blunt state based on the first resistance value and the second resistance value. The determining unit 60 calculates a ratio of the first resistance value R1 to the second resistance value R2 (R1/R2) acquired (Step S 21). The determining unit 60 compares the ratio of the first resistance value to the second resistance value R1/R2 with the predetermined threshold (Step S 22).

The determining unit 60 determines that the detecting unit 10 is in the blunt state (Step S 23) if the ratio R1/R2 is greater than the given threshold (Step S 22: YES). On the contrary, the determining unit 60 determines that the detecting unit 10 is not in the blunt state (Step S 24) if the ratio R1/R2 is equal to or smaller than the given threshold (Step S 22: NO). Since the ratio of the first resistance value to the second resistance value is less affected by a variability of the sensor resistance value among the products, a more accurate determination can be made by determining as to the blunt state based on the ratio of the first resistance value to the second resistance value.

Figure 12:
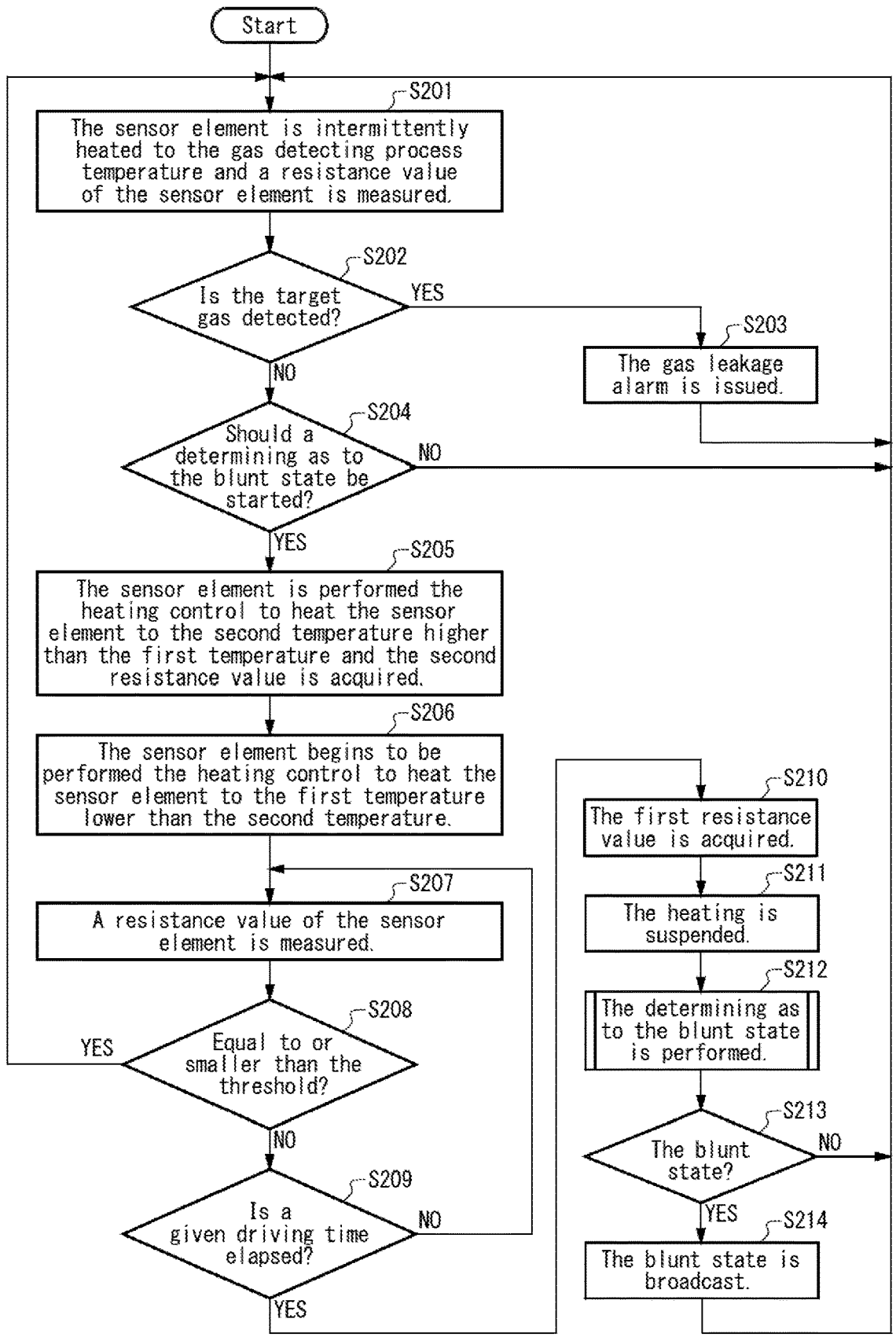
FIG. 12 is an example of a flow chart showing a process by the gas alarm 100 according to the second embodiment of the present invention.

FIG. 12 is an example of a flow chart showing a process by the gas alarm 100 according to the second embodiment of the present invention. In the gas alarm 100 according to the first embodiment above described, in detecting the target gas, heating the sensor resistor 12 to the gas detecting process temperature was used as heating the sensor resistor 12 to the second temperature. However, heating the sensor resistor 12 to the gas detecting process temperature and heating the sensor resistor 12 to the second temperature may be separately provided. The gas alarm 100 according to the second embodiment has a similar structure to that of the gas alarm 100 according to the first embodiment with the exception that a part of the controlling differs. Steps S 201 to S 204 are similar to Steps S 101 to S 104 in FIG. 9. The steps of Step S 207 to S 214 are similar to those of Steps S 106 to S 113 in FIG. 9. Hence, the description thereof is not repeated here.

The heating control unit 30 waits until when the determining as to the blunt state should be started to run (Step S 204: YES) and then, the heating control unit 30 heats intermittently the sensor resistor 12 until a temperature of the sensor resistor 12 reaches the second temperature higher than the first temperature (Step S 205). The heating control unit 30 then begins to perform the heating control for the heater 14 to heat the sensor resistor 12 to the first temperature lower than the second temperature (Step S 206). The influence of the miscellaneous gas can be evaluated accurately by first heating the sensor resistor 12 to the second temperature higher than the first temperature so as to have oxygen absorbed ($O^{2-}$ absorption) on the surface of the sensing layer of the sensor resistor 12, performing the heating control to heat the sensor resistor 12 to the first temperature, and then evaluating the influence of the miscellaneous gas.

Figure 13:
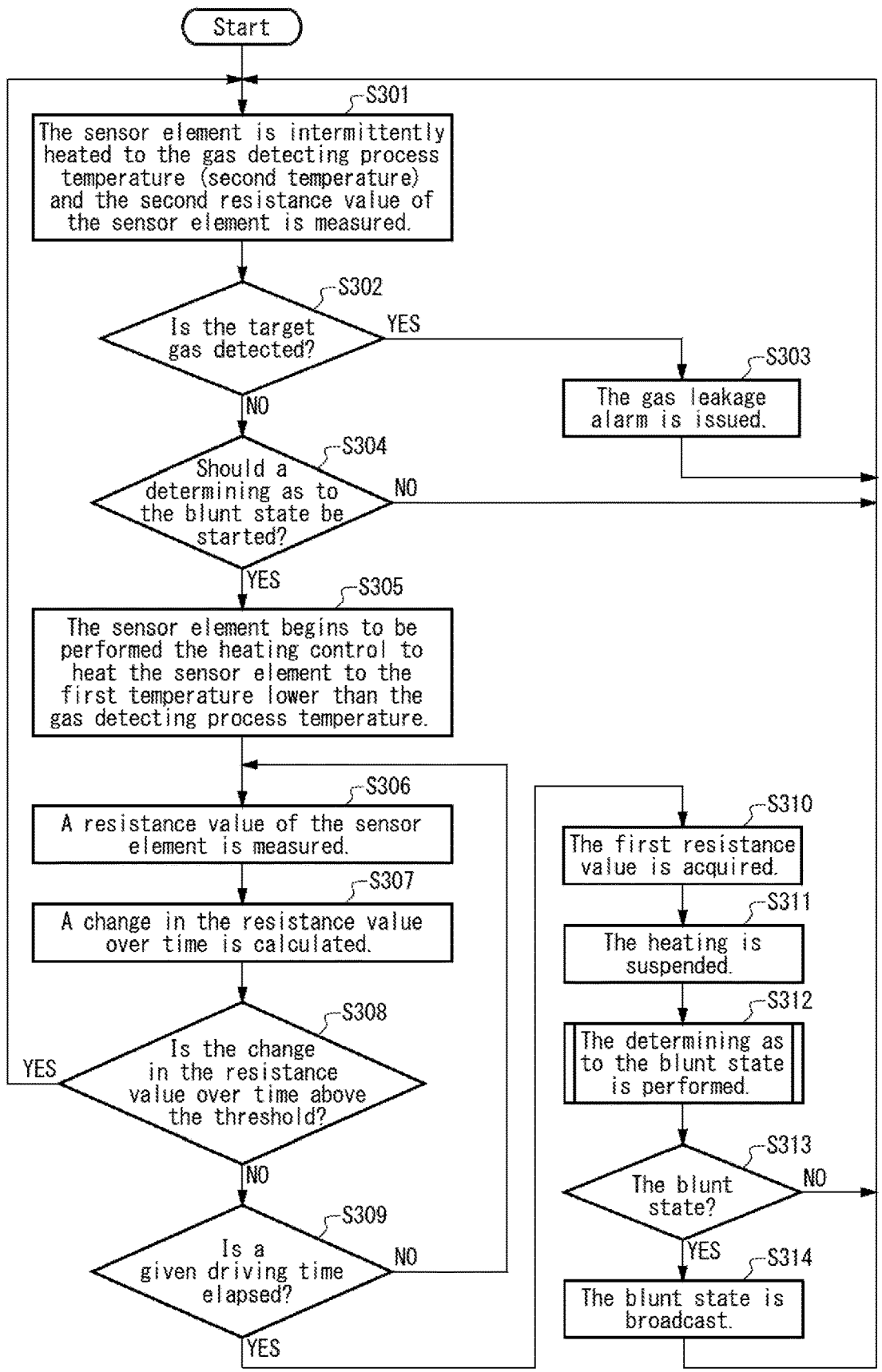
FIG. 13 is an example of a flow chart showing a process by the gas alarm 100 according to the third embodiment of the present invention.

FIG. 13 is an example of a flow chart showing a process by the gas alarm 100 according to the third embodiment of the present invention. In the gas alarms 100 according to the first and second embodiments, the case in which the aborting control unit 70 aborts the heating process to determine whether the sensor resistor 12 is in the blunt state when a resistance value of the sensor resistor 12 is equal to or smaller than the predetermined threshold is described. However, the aborting process is not limited to this case. The gas alarm 100 of this example has a similar configuration to those of the gas alarms 100 according to the first and second embodiments with the exception that a part of the aborting process by the aborting control unit 70 differs. The steps of Steps S 301 to S 306 of FIG. 13 are similar to those of Steps S 101 to S 106 of FIG. 9. In addition, the steps of Steps S 309 to S 314 of FIG. 13 are similar to those of Steps S 108 to S113 of FIG. 9.

The aborting control unit 70 calculates a change in the sensor resistance value over time (Step S 307). Then the aborting control unit 70 aborts the heating process to determine whether the sensor resistor 12 is in the blunt state based on an inclination of a change in the resistance value of the sensor resistor 12 over time measured by the measuring unit 20 after beginning of the heating process by the heating control unit 30 (Step S 305). As shown in FIG. 5, immediately after heating the sensor resistor 12 to the second temperature, a sensor resistance value in the clean environment and a sensor resistance value in the environment including the miscellaneous gas show the similar values, and thereafter in the course of performing the heating control to heat the sensor resistor 12 to the first temperature, a sensor resistance value in the environment including the miscellaneous gas drops abruptly compared to a sensor resistance value in the clean environment. Accordingly, a change in the sensor resistance value over time in the environment including the miscellaneous gas is larger than a change in the sensor resistance value over time in the clean environment.

The aborting control unit 70 determines whether a change in the sensor resistance value over time is above the threshold (Step S 308). The aborting control unit 70 aborts the heating process to determine whether the sensor resistor 12 is in the blunt state if a change in the sensor resistance value over time is above the threshold (Step S 308: YES). The process returns to Step S 301. Accordingly, this can stop the heating process at the first temperature where the miscellaneous gas cannot be combusted enough in the selective combustion layer 9.

On the contrary, because it can be considered that the miscellaneous gas is not detected if a change in the sensor resistance value over time is equal to or smaller than the threshold (Step S 308: NO), any problems will not occur if the heating control to the first temperature is continued. Hence, waiting until when a predetermined heater driving time is elapsed (Step S 309: YES), the first acquiring unit 52 acquires the sensor resistance value measured by the measuring unit 20 where a temperature of the sensor resistor 12 reaches the first temperature as the first resistance value (Step S 310). Then the heating control unit 30 suspends the heating (Step S 311). The determining unit 60 runs the determining as to the blunt state (Step S 312).

Figure 14:
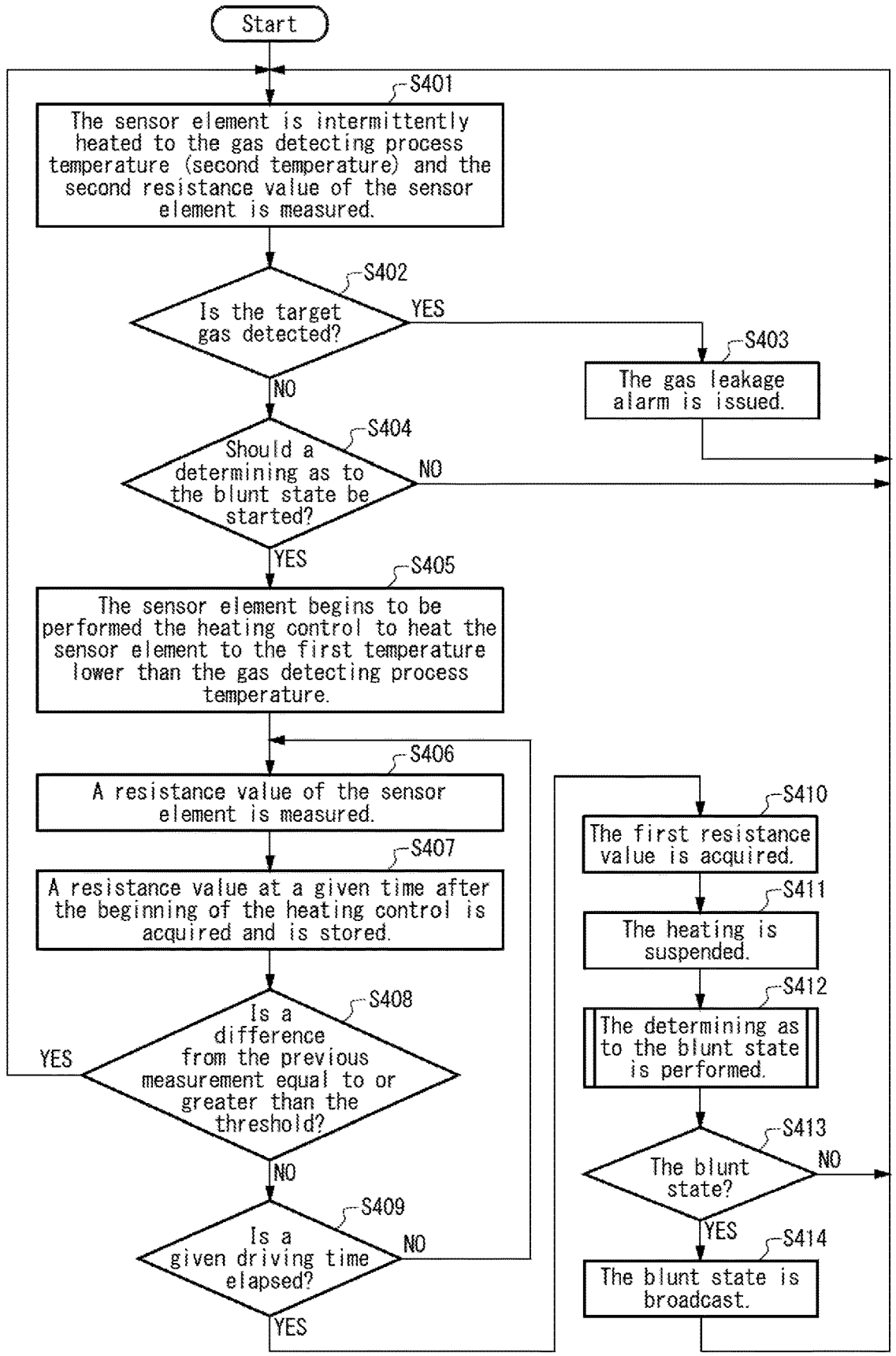
FIG. 14 is an example of a flow chart showing a process by the gas alarm 100 according to the fourth embodiment of the present invention.

FIG. 14 is an example of a flow chart showing a process by the gas alarm 100 according to the fourth embodiment of the present invention. The gas alarm 100 of this example has a similar configuration to those of the gas alarms 100 according to the first to third embodiments with the exception that a part of the aborting process by the aborting control unit 70 differs. The steps of Steps S 401 to S 406 of FIG. 14 are similar to those of Steps S 101 to S 106 of FIG. 9. In addition, the steps of Steps S 409 to S 414 of FIG. 13 are similar to those of Steps S 108 to S 113 of FIG. 9.

After the heating control to the first temperature is begun, the measuring unit 20 still measures a sensor resistance value of the sensor resistor 12 (Step S 406). Then the aborting control unit 70 acquires a sensor resistance value measured by the measuring unit 20 at the time when a given time is elapsed after beginning of the heating process by the heating control unit 30 and stores it in the memory unit 80 (Step S 407). The aborting control unit 70 may read the previous sensor resistance value from the memory unit 80 and compare the sensor measurement value currently measured with the previous sensor resistance value.

The aborting control unit 70 aborts the heating process to determine whether the sensor resistor 12 is in the blunt state based on the result of comparing the sensor resistance value of the sensor resistor 12 measured by the measuring unit 20 after beginning of the heating process by the heating control unit 30 with the previously measured sensor resistance value. In an example, the aborting control unit 70 calculates a difference between the previous sensor resistance value and the sensor measurement value currently measured. If the difference is equal to or greater than the threshold value (Step S 408: YES), the aborting control unit 70 aborts the heating process to determine the sensor resistor 12 is in the blunt state. The process returns to Step S 401.

On the contrary, if the difference calculated is below the threshold (Step S 408: NO), any particular problems will not occur if the heating control to the first temperature is continued. Thus, the heating process to determine whether the sensor resistor 12 is in the blunt state is continued. In the case where the miscellaneous gas was not detected at the previous measurement but it is detected at the current measurement, since a sensor resistance value changes substantially when a certain time is elapsed after beginning of the heating control to the first temperature, the difference between the previous sensor resistance value and the sensor measurement value currently measured is large.

As shown in FIG. 5, when time is not elapsed long enough after beginning of the heating control to the first temperature, it is difficult to differentiate between a sensor resistance value in the environment including the miscellaneous gas and a sensor resistance value in the clean environment. On the other hand, when time is elapsed too long after beginning of the heating control to the first temperature, the heating process to the first temperature causes the oxygen ions ($O^{2-}$) absorbed on the surface of the sensing layer functioning as the sensor resistor 12 to desorb excessively. Accordingly, the sensor resistance value measured at the time ranging from 5 sec to 10 sec after beginning of the heating control to the first temperature may be acquired.

Figure 15:
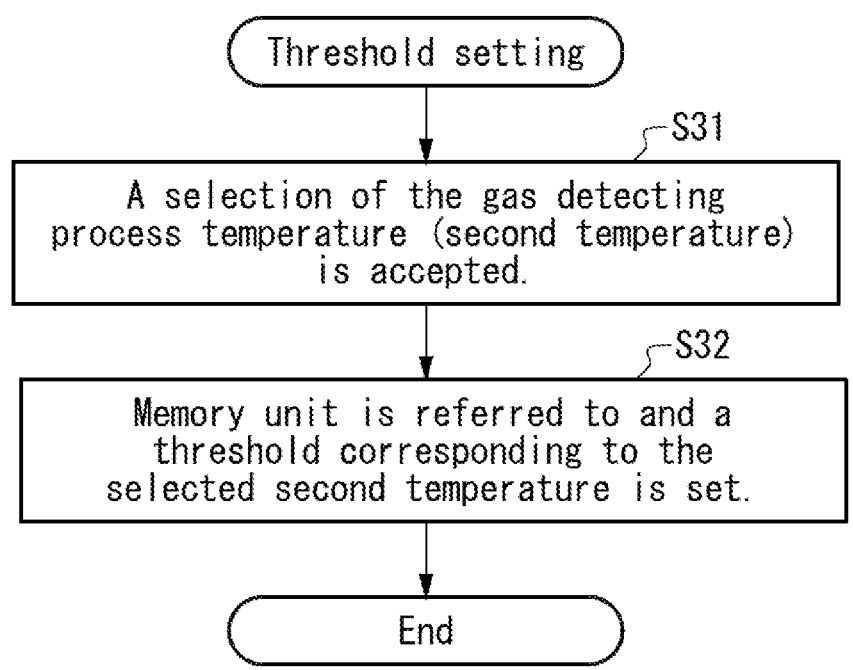
FIG. 15 is a flow chart showing a threshold setting process by the gas alarm 100 according to the fifth embodiment of the present invention.

FIG. 15 is a flow chart showing a threshold setting process by the gas alarm 100 according to the fifth embodiment of the present invention. The gas alarm 100 according to the fifth embodiment is similar to the gas alarms 100 according to the first to fourth embodiments except that a plurality of second temperatures can be set and the memory unit 80 stores different thresholds for different ones of the plurality of second temperatures. The other structures and the controlling are similar to those of the gas alarms 100 according to the first to the fourth embodiments. The control device 200 accepts a selection of the gas detecting process temperatures (the second temperatures) (Step S 31). For example, the control device 200 may switch the second temperatures depending on the target gases to be detected. Users can select a second temperature from the candidates of the plurality of second temperatures.

Once a second temperature is selected, the aborting control unit 70 refers to the memory unit 80 and reads the threshold corresponding to the selected second temperature. The aborting control unit 70 sets the threshold read as a threshold to be compared with a sensor resistance value in order to determine to abort the heating process (Step S 32). For example, a table for matching between a plurality of gas detecting process temperatures and thresholds is stored beforehand in the memory unit 80. According to the gas alarm 100 of this example, a second temperature can be selected from the plurality of second temperatures and a threshold matching the selected second temperature can be set.

Figure 16:
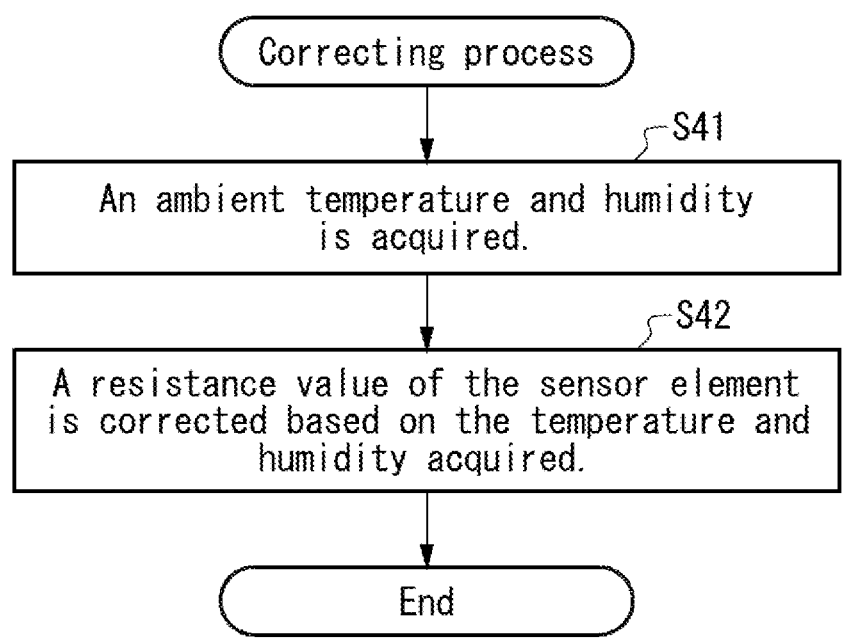
FIG. 16 is a flow chart showing a correcting process by the gas alarm 100 according to the sixth embodiment of the present invention.

FIG. 16 is a flow chart showing a correcting process by the gas alarm 100 according to the sixth embodiment of the present invention. The gas alarm of this example has an additional correcting feature to account for a temperature and humidity influence when compared with the gas alarms 100 of the first to fifth embodiments. The other structures and the controlling are similar to those of the gas alarms 100 according to the first to the fifth embodiments. A sensor resistance value varies depending on a temperature and humidity.

The temperature and humidity measurement unit 92 may use the detecting unit 10 itself measuring at least one of a temperature and a humidity at or near the gas alarm 100 (Step S 41) as the temperature and humidity measurement unit 92. More specifically, the detecting unit 10 may detect the ambient air humidity based on a sensor resistance value during the stop of power supply to the heater 14 which is from stop until resumption of power supply to the heater 14. For example, in the temperature area ranging from 50° C. to 250° C., the higher a relative humidity is and the larger an amount of water vapor absorption is, the smaller a sensor resistance value of the sensor resistor 12 becomes. Accordingly, a relative humidity may be detected from a sensor resistance value in the temperature area ranging from 50° C. to 250° C.

The correcting unit 90 corrects the first resistance value and the second resistance value depending on a measurement result by the temperature and humidity measurement unit 92 (Step S 42). In an example, the correcting unit 90 refers to the memory unit 80 and reads a correcting factor corresponding to the measurement result by the temperature and humidity measurement unit 92. A relationship between a temperature and humidity and a sensor resistance value may be measured beforehand and then a table or a converting expression which matches a temperature and humidity to a correcting factor based on the measurement result may be stored on the memory unit 80. A correcting factor for the first resistance value and a correcting factor for the second resistance value may be separately prepared.

The correcting unit 90 corrects the first resistance value and the second resistance value using the correcting factor read. The correcting unit 90 may calculate the corrected first resistance value and the corrected second resistance value by multiplying the first resistance value and the second resistance value by the correcting factor, respectively. The determining unit 60 may determine whether the sensor resistor 12 becomes in the blunt state or not based on the corrected first resistance value. The determining unit 60 may determine whether the sensor resistor 12 becomes in the blunt state or not based on the corrected first resistance value and the corrected second resistance value. In particular, the determining unit 60 may determine whether the sensor resistor 12 becomes in the blunt state or not based on a ratio of the corrected first resistance value to the corrected second resistance value.

According to the gas alarm 100 of this example, at least one of a temperature and a humidity is measured and the sensor resistor 12 can be determined to be in the blunt state considering the influence thereby enabling a more accurate determination as to the blunt state.

Figure 17:
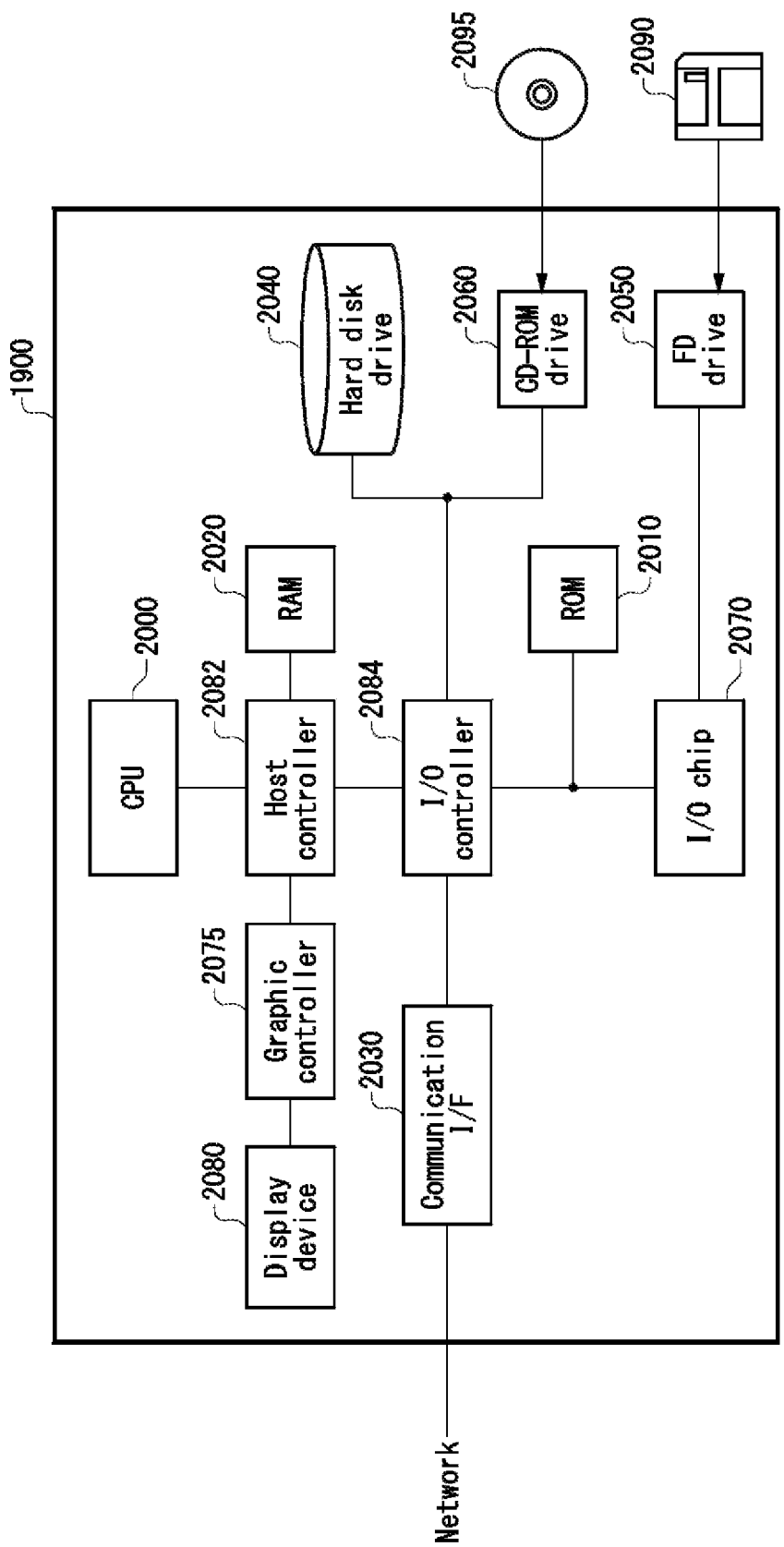
FIG. 17 shows an example of hardware configuration of a computer 1900 according to one embodiment of the present invention.

FIG. 17 shows an example of hardware configuration of a computer 1900 according to an embodiment of the present invention. The computer 1900 according to this embodiment is a micro-computer, for example. The computer 1900 includes a CPU peripheral unit comprising a CPU 2000, a RAM 2020, a graphic controller 2075 and a display device 2080 which are interconnected by a host controller 2082, an input/output unit comprising a communication interface 2030, a hard disk drive 2040 and a CD-ROM drive 2060 which are connected to the host controller 2082 by an input/output controller 2084, and a legacy input/output unit comprising a ROM 2010, a flexible disk drive 2050 and an input/output chip 2070 which are connected to the input/output controller 2084.

The host controller 2082 connects the RAM 2020 to the CPU 2000 and the graphic controller 2075 which access to the RAM 2020 at a high transfer rate. The CPU 2000 operates based on programs which are stored on the ROM 2010 and the RAM 2020 and controls each unit. The graphic controller 2075 acquires image data generated on a frame buffer created in the RAM 2020 by the CPU 2000 and so forth and displays it on the display device 2080. Instead of this, the graphic controller 2075 may have a frame buffer therein for storing image data generated by the CPU 2000 and so forth.

The input/output controller 2084 connects the communication interface 2030, the hard disk drive 2040, and the CD-ROM drive 2060 which are relatively fast input/output devices to the host controller 2082. The communication interface 2030 communicates with other devices over the network. The hard disk drive 2040 stores programs and data used by the CPU 2000 in the computer 1900. The CD-ROM drive 2060 reads the programs or data from the CD-ROM 2095 and provides them to the hard disk drive 2040 via the RAM 2020.

In addition, relatively slow input/output devices such as the ROM 2010, the flexible disk drive 2050 and the input/output chip 2070 are connected to the input/output controller 2084. The ROM 2010 stores a boot program which the computer 1900 runs at start-up and/or programs and so forth depending on the hardware of the computer 1900. The flexible disk drive 2050 reads the programs or data from the flexible disk 2090 and provides them to the hard disk drive 2040 via the RAM 2020. The input/output chip 2070 connects the flexible disk drive 2050 to the input/output controller 2084 and also connects various input/output devices to the input/output controller 2084 via, for example, a parallel port, a serial port, a keyboard port and a mouse port and so forth.

The programs provided to the hard disk drive 2040 via the RAM 2020 are stored on recording media such as the flexible disk 2090, the CD-ROM 2095 or the IC card and so forth and then provided by users. The programs are read from the recording media and installed into the hard disk drive 2040 in the computer 1900 via the RAM 2020 and then run by the CPU 2000.

The program installed in the computer 1900 and causing the computer 1900 to operate as a control device 200 causes the computer 1900 to perform operations including: measuring a characteristic value of the sensor resistor 12, controlling the heater 14 to perform the heating process to heat the sensor resistor 12, determining based on the characteristic value whether the sensor resistor 12 is in the blunt state in which sensitivity of the sensor resistor 12 is decreased, and aborting the heating process to determine whether the sensor resistor 12 is in the blunt state when the characteristic value of the sensor resistor 12 measured after beginning of the heating process to determine whether the sensor resistor 12 is in the blunt state meets the predetermined condition. More specifically the program causes the computer 1900 to perform operations of measuring a resistance value of the sensor resistor 12, controlling the heater 14 to perform the heating process to heat the sensor 12 to the first temperature lower than the detecting process temperature, acquiring the first resistance value of the sensor resistor 12 measured where a temperature of the sensor resistor 12 reaches the first temperature, determining whether the sensor resistor 12 is in the blunt state in which sensitivity of the sensor resistor 12 is decreased based on the first resistance value, and aborting the heating process to determine whether the sensor resistor 12 is in the blunt state when the resistance value of the sensor resistor 12 measured after beginning of the heating process to determine whether the sensor resistor 12 is in the blunt state meets the predetermined condition. The program causes the computer 1900 to function as a measuring unit 20, a heating control unit 30, an alarm generation unit 40, a first acquiring unit 52, a second acquiring unit 54, a determining unit 60, an aborting control unit 70, a memory unit 80, and a correcting unit 90.

When loaded in the computer 1900, the information processing written in the program functions as implemented means which are achieved by cooperation of the software program and the various above-described hardware resources, such as the measuring unit 20, the heating control unit 30, the alarm generation unit 40, the first acquiring unit 52, the second acquiring unit 54, the determining unit 60, the aborting control unit 70, the memory unit 80, and the correcting unit 90. These implemented means construct the control device 200 particularly suitable for a use purpose by achieving information operations or processing depending on the use purpose of the computer 1900 in this embodiment.

As an example, when the computer 1900 communicates with external devices and so forth, the CPU 2000 executes a communication program loaded on the RAM 2020 and indicates communication processing to the communication interface 2030 based on the processes written in the communication program. Under the control of the CPU 2000, the communication interface 2030 reads data for transmission stored in a send buffer area and so forth created in a storage device such as the RAM 2020, the hard disk drive 2040, the flexible disk 2090 or the CD-ROM 2095 and sends the data to the network, or writes received data from the network to a receive buffer area and so forth created in the storage device. In this manner, the communication interface 2030 may transfer data to be sent and received from and to the storage device by means of direct memory access (DMA), or instead of this, the CPU 2000 may read data from the storage device or the communication interface 2030 which transferred the data and may transfer the data to be sent and received to the communication interface 2030 or the storage device which are to transferred the data by writing the data thereto.

In addition, the CPU 2000 causes all or necessary part of files or database stored in an external storage device such as the hard disk drive 2040, the CD-ROM drive 2060 (CD-ROM 2095), and the flexible disk drive 2050 (flexible disk 2090) to be loaded into the RAM 2020 by means of DMA transfer and so forth, and then performs various operations on the data in the RAM 2020. Then the CPU 2000 writes back the data processed to the external storage device by means of DMA transfer and so forth. In this process, the RAM 2020 can be considered to temporarily maintain contents of the external storage device, therefore in this embodiment, the RAM 2020 and the external storage device and the like shall be collectively referred to as memory, a memory unit or a storage device and so forth. Various programs and various information such as data, a table, and database in this embodiment are stored on the storage device as such and are subject to information processing. The CPU 2000 can maintain a part of the RAM 2020 in a cache memory and read and write on the cache memory. The cache memory is also responsible for a part of the function of the RAM 2020 in this form, thus the cache memory shall be included in the RAM 2020, the memory and/or the storage device in this embodiment unless otherwise specifically stated.

Moreover, the CPU 2000 performs various operations including various calculations, information processing, conditional determinations, and information searches/replaces described in this embodiment, which are specified by a sequence of programming instructions on the data read from the RAM 2020 and writes back the data to the RAM 2020. For example, in the case of the conditional determinations, the CPU 2000 determines whether or not various variables indicated in this embodiment meet a condition such as "greater than", "smaller than", "equal to or greater than", "equal to or smaller than", and "equal to" and so forth by comparing those to other variables or constants, and if the condition is met (or not met), the CPU 2000 branches it to a different sequence of the instructions or calls a sub-routine.

Moreover, the CPU 2000 can search for information stored in the files or database and so forth in the storage device. For example, in the case where several entries in which the attribute values of the first attributes are associated with the attribute values of the second attributes, respectively are stored in the storage device, the CPU 2000 can search an entry whose attribute value of the first attribute matches the specified condition among the several entries stored in the storage device, and read the attribute value of the second attribute stored in the entry thereby obtaining the attribute value of the second attribute associated with the first attribute which meets the given condition.

The programs or modules above mentioned may be stored in external recording media. For recording media, other than the flexible disk 2090, CD-ROM 2095, optical recording media such as DVDs or CDs and so forth, magneto-optical recording media such as MOs and so forth, tape media, and semiconductor memory such as IC cards and so forth can be used. The programs may also be provided to the computer 1900 over the network using the storage device as the recording media like hard disks or RAMs and so forth provided in server system connected to a dedicated communication network or the internet.

Although the present invention has been described by means of embodiments above, each embodiment herein can be combined as appropriate. The technical scope of the present invention should not be construed to be limited to the scope of the embodiments above mentioned. It is apparent to those skilled in the art that various alterations or improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

2; silicon substrate, 3; thermal insulating support layer, 4; electrical insulating layer, 5; gas sensing layer, 6; through-hole, 7; joint layer, 8; electrode of the gas sensing layer, 9; selective combustion layer, 10; detecting unit, 12; sensor resistor, 14; heater, 20; measuring unit, 30; heating control unit, 40; alarm generation unit, 52; first acquiring unit, 54; second acquiring unit, 60; determining unit, 70; aborting control unit, 80; memory unit, 90; correcting unit, 92; temperature and humidity measurement unit, 100; gas alarm; 200 control device, 101; sensor resistance characteristic, 102; sensor resistance characteristic, 103; sensor resistance characteristic, 1900; computer, 2000; CPU, 2010; ROM, 2020; RAM, 2030; communication interface, 2040; hard disk drive, 2050; flexible disk drive, 2060; CD-ROM drive, 2070; input/output chip, 2075; graphic controller, 2080; display device, 2082; host controller, 2084; input/output controller, 2090; flexible disk, 2095; CD-ROM.

What is claimed is:

1. A gas alarm including a sensor element and a heater to heat the sensor element and detecting a target gas based on a characteristic value of the sensor element heated to a detecting process temperature by the heater, the gas alarm comprising:

a measuring unit to measure a characteristic value of the sensor element;

a heating control unit to control the heater to routinely perform a first heating process to heat the sensor element to the detecting process temperature and perform a second heating process to heat the sensor element to a first temperature lower than the detecting process temperature between instances of the first heating process;

a determining unit to determine, at least based on the characteristic value measured at the first temperature, whether the sensor element is in a blunt state in which sensitivity of the sensor element is decreased; and an aborting control unit to abort the second heating process before the sensor element reaches the first temperature, so as to cause the heating control unit to perform the first heating process to heat the sensor element to the detecting process temperature, when the characteristic value of the sensor element measured at a temperature between the detecting process temperature and the first temperature meets a predetermined condition, wherein the second heating process is allowed to continue when the characteristic value of the sensor element measured at the temperature between the detecting process temperature and the first temperature does not meet the predetermined condition.

2. The gas alarm according to claim 1, wherein, the measuring unit measures a resistance value of the sensor element; and the gas alarm comprising a first acquiring unit to acquire a first resistance value of the sensor element measured by the measuring unit where a temperature of the sensor element reaches the first temperature, wherein, the determining unit determines, based on the first resistance value, whether the sensor element is in the blunt state in which the sensitivity of the sensor element is decreased; and the aborting control unit aborts the second heating process to determine whether the sensor element is in the blunt state when a resistance value of the sensor element measured by the measuring unit at the temperature between the detecting process temperature and the first temperature meets a predetermined condition.

3. The gas alarm according to claim 2, further comprising a second acquiring unit to acquire a second resistance value of the sensor element measured by the measuring unit where the temperature of the sensor element is a second temperature higher than the first temperature, wherein,
the determining unit determines whether the sensor element is in the blunt state based on the first resistance value and the second resistance value.

4. The gas alarm according to claim 3, wherein the determining unit determines whether the sensor element is in the blunt state by comparing a ratio of the first resistance value to the second resistance value with a predetermined threshold.

5. The gas alarm according to claim 3,
wherein,
the heating control unit performs a heating control such that the temperature of the sensor element becomes the first temperature after performing a heating control such that the temperature of the sensor element becomes the second temperature; and
the first acquiring unit acquires the first resistance value after the second acquiring unit acquires the second resistance value.

6. The gas alarm according to claim 2, wherein the aborting control unit aborts the second heating process to determine whether the sensor element is in the blunt state when the resistance value of the sensor element measured at the temperature between the detecting process temperature and the first temperature is equal to or smaller than a predetermined threshold.

7. The gas alarm according to claim 6, wherein a resistance value of the sensor element at a time when the sensor element not in the blunt state is stabilized at the first temperature in a clean environment is set as the threshold.

8. The gas alarm according to claim 6, wherein a resistance value higher than that of the sensor element at a time when the sensor element not in the blunt state is stabilized at the first temperature in a clean environment is set as the threshold.

9. The gas alarm according to claim 3, wherein,
the aborting control unit is to abort the second heating process to determine whether the sensor element is in the blunt state when the resistance value of the sensor element measured at the temperature between the detecting process temperature and the first temperature is equal to or smaller than a predetermined threshold,
the gas alarm allowing the second temperature to be set to one of a plurality of predetermined temperatures, and comprising a memory unit to store a threshold for each of the plurality of predetermined temperatures.

10. The gas alarm according to claim 2, wherein the aborting control unit aborts the second heating process to determine whether the sensor element is in the blunt state based on an inclination of a change in the resistance value of the sensor element over time measured at temperatures between the detecting process temperature and the first temperature.

11. The gas alarm according to claim 2, wherein the aborting control unit aborts the second heating process to determine whether the sensor element is in the blunt state, based on a result of comparing the resistance value of the sensor element measured at the temperature between the detecting process temperature and the first temperature with a previously measured resistance value.

12. The gas alarm according to claim 3, further comprising:
a temperature and humidity measurement unit to measure at least one of a temperature and a humidity at or near the gas alarm; and
a correcting unit to correct the first resistance value and the second resistance value depending on a measurement result by the temperature and humidity measurement unit,
wherein,
the determining unit determines whether the sensor element is in the blunt state based on the corrected first resistance value and the corrected second resistance value.

13. A control device in a gas alarm including a sensor element and a heater to heat the sensor element and detecting a target gas based on a characteristic value of the sensor element heated to a detecting process temperature by the heater, the control device comprising:
a measuring unit to measure a characteristic value of the sensor element;
a heating control unit to control the heater to routinely perform a first heating process to heat the sensor element to the detecting process temperature and perform a second heating process to heat the sensor element to a first temperature lower than the detecting process temperature between instances of the first heating process;
a determining unit to determine, at least based on the characteristic value measured at the first temperature, whether the sensor element is in a blunt state in which sensitivity of the sensor element is decreased; and
an aborting control unit to abort the second heating process before the sensor element reaches the first temperature, so as to cause the heating control unit to perform the first heating process to heat the sensor element to the detecting process temperature, when the characteristic value of the sensor element measured at a temperature between the detecting process temperature and the first temperature meets a predetermined condition,
wherein the second heating process is allowed to continue when the characteristic value of the sensor element measured at the temperature between the detecting process temperature and the first temperature does not meet the predetermined condition.

14. A computer program product having computer instructions, recorded on a non-transitory computer readable medium, for enabling a computer executing the computer instructions to perform operations, the computer controlling a gas alarm which includes a sensor element and a heater to heat the sensor element and detects a target gas based on a characteristic value of the sensor element heated to a detecting process temperature by the heater,
the operations comprising:
measuring a characteristic value of the sensor element;

controlling the heater to routinely perform a first heating process to heat the sensor element to the detecting process temperature and perform a second heating process to heat the sensor element to a first temperature lower than the detecting process temperature between instances of the first heating process;

determining, at least based on the characteristic value measured at the first temperature, whether the sensor element is in a blunt state in which sensitivity of the sensor element is decreased; and aborting the second heating process before the sensor element reaches the first temperature, so as to cause the controlling to perform the first heating process to heat the sensor element to the detecting process temperature, when the characteristic value of the sensor element measured at a temperature between the detecting process temperature and the first temperature meets a predetermined condition, wherein the second heating process is allowed to continue when the characteristic value of the sensor element measured at the temperature between the detecting process temperature and the first temperature does not meet the predetermined condition.

* * * * *